United States Patent
Nakayama et al.

(10) Patent No.: US 10,439,150 B2
(45) Date of Patent: Oct. 8, 2019

(54) LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Tomonori Nakayama, Kanagawa (JP); Takako Takasu, Kanagawa (JP); Satoko Shitagaki, Kanagawa (JP); Harue Osaka, Kanagawa (JP); Toshiki Hamada, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 62 days.

(21) Appl. No.: 15/350,822

(22) Filed: Nov. 14, 2016

(65) Prior Publication Data

US 2017/0125705 A1 May 4, 2017

Related U.S. Application Data

(63) Continuation of application No. 14/029,208, filed on Sep. 17, 2013, now Pat. No. 9,502,666.

(30) Foreign Application Priority Data

Sep. 21, 2012 (JP) ................. 2012-208080

(51) Int. Cl.
| | |
|---|---|
| *H01L 51/00* | (2006.01) |
| *C09K 11/06* | (2006.01) |
| *H05B 33/14* | (2006.01) |
| *C07D 487/14* | (2006.01) |
| *C09K 11/02* | (2006.01) |
| *H01L 51/50* | (2006.01) |

(52) U.S. Cl.
CPC ........ *H01L 51/0072* (2013.01); *C07D 487/14* (2013.01); *C09K 11/025* (2013.01); *C09K 11/06* (2013.01); *H01L 51/0071* (2013.01); *H01L 51/0074* (2013.01); *H01L 51/0085* (2013.01); *H05B 33/14* (2013.01); *C09K 2211/1007* (2013.01); *C09K 2211/1029* (2013.01); *C09K 2211/1059* (2013.01); *C09K 2211/185* (2013.01); *H01L 51/0058* (2013.01); *H01L 51/0067* (2013.01); *H01L 51/5004* (2013.01); *H01L 51/5016* (2013.01); *H01L 2251/552* (2013.01)

(58) Field of Classification Search
CPC ............ C09K 11/06; H01L 51/0072
See application file for complete search history.

(56) References Cited

U.S. PATENT DOCUMENTS

| | | |
|---|---|---|
| 6,097,147 A | 8/2000 | Baldo et al. |
| 6,492,526 B1 | 12/2002 | Christou et al. |
| 6,830,828 B2 | 12/2004 | Thompson et al. |
| 6,902,830 B2 | 6/2005 | Thompson et al. |
| 7,001,536 B2 | 2/2006 | Thompson et al. |
| 7,291,406 B2 | 11/2007 | Thompson et al. |
| 7,452,615 B2 | 11/2008 | Kim et al. |
| 7,537,844 B2 | 5/2009 | Thompson et al. |
| 7,601,859 B2 | 10/2009 | Christou |
| 7,883,787 B2 | 2/2011 | Thompson et al. |
| 7,906,226 B2 | 3/2011 | Matsuura et al. |
| 8,105,701 B2 | 1/2012 | Matsuura et al. |
| 8,470,455 B2 | 6/2013 | Matsuura et al. |
| 8,557,402 B2 | 10/2013 | Thompson et al. |

(Continued)

FOREIGN PATENT DOCUMENTS

| | | |
|---|---|---|
| CN | 101023148 A | 8/2007 |
| CN | 101371377 A | 2/2009 |

(Continued)

OTHER PUBLICATIONS

Taiwanese Office action for Application No. 102133176 dated Dec. 19, 2016.*
Chinese Office Action re Application No. CN 201380048942.0, dated Jan. 18, 2017.
Franceschin, M. et al., "Study of a Convenient Method for the Preparation of Hydrosoluble Fluorescent Triazatruxene Derivatives," European Journal of Organic Chemistry, 2010, vol. 2010, No. 1, pp. 134-141.
Phillips, D.P. et al., "Copper-Catalyzed N-arylation of Oxindoles," Tetrahedron Letters, Oct. 1, 2006, vol. 47, No. 40, pp. 7137-7138.
International Search Report re Application No. PCT/JP2013/075397, dated Dec. 10, 2013.

(Continued)

*Primary Examiner* — Kuo Liang Peng
(74) *Attorney, Agent, or Firm* — Husch Blackwell LLP

(57) ABSTRACT

A light-emitting element emitting phosphorescence and having high emission efficiency, in which a property of injecting holes to a light-emitting layer is increased, is provided. The light-emitting layer of the light-emitting element includes a first organic compound represented by the following general formula (G1) and a second organic compound which is a phosphorescent compound. The difference between the HOMO level of the first organic compound and the HOMO level of the second organic compound is lower than or equal to 0.3 eV.

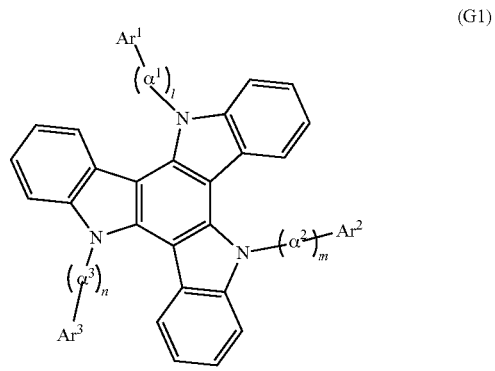

(G1)

18 Claims, 13 Drawing Sheets

(56) References Cited

U.S. PATENT DOCUMENTS

| | | | |
|---|---|---|---|
| 8,574,726 B2 | 11/2013 | Thompson et al. | |
| 8,841,653 B2 | 9/2014 | Shitagaki et al. | |
| 8,877,350 B2 | 11/2014 | Spindler et al. | |
| 9,209,415 B2 | 12/2015 | Shitagaki et al. | |
| 9,502,666 B2* | 11/2016 | Nakayama | H01L 51/0071 |
| 2006/0063037 A1* | 3/2006 | Kim | C07D 487/14 |
| | | | 428/690 |
| 2008/0129195 A1* | 6/2008 | Ishizaki | H01L 27/322 |
| | | | 313/504 |
| 2009/0295276 A1* | 12/2009 | Asari | C09K 11/06 |
| | | | 313/504 |
| 2011/0031482 A1 | 2/2011 | Furukawa et al. | |
| 2011/0062429 A1 | 3/2011 | Kai et al. | |
| 2012/0080656 A1 | 4/2012 | Choi et al. | |
| 2013/0075705 A1 | 3/2013 | Takasu et al. | |
| 2013/0200340 A1 | 8/2013 | Otsu et al. | |
| 2014/0008639 A1 | 1/2014 | Thompson et al. | |

FOREIGN PATENT DOCUMENTS

| | | |
|---|---|---|
| CN | 101901875 A | 12/2010 |
| CN | 101919083 A | 12/2010 |
| CN | 102017220 A | 4/2011 |
| CN | 102449800 A | 5/2012 |
| EP | 1 729 327 A1 | 12/2006 |
| EP | 1 933 395 A1 | 6/2008 |
| EP | 1 956 666 A1 | 8/2008 |
| EP | 2 270 895 A2 | 1/2011 |
| EP | 2 278 637 A1 | 1/2011 |
| EP | 2 284 920 A1 | 2/2011 |
| EP | 2 306 495 A1 | 4/2011 |
| EP | 2 623 508 A1 | 8/2013 |
| EP | 2 911 211 A1 | 8/2015 |
| EP | 3 076 759 A1 | 10/2016 |
| JP | 2001-261680 A | 9/2001 |
| JP | 2004-055240 A | 2/2004 |
| JP | 2004-123619 A | 4/2004 |
| JP | 2008-513441 | 5/2008 |
| JP | 2010-182699 A | 8/2010 |
| JP | 2011-054931 A | 3/2011 |
| JP | 2011-077032 A | 4/2011 |
| JP | 4734333 B2 | 7/2011 |
| JP | 4819181 B2 | 11/2011 |
| JP | 2013-177361 A | 9/2013 |
| KR | 2006-0051418 A | 5/2006 |
| KR | 2011-0010750 A | 2/2011 |
| KR | 2012-0033711 A | 4/2012 |
| KR | 2012-0033722 A | 4/2012 |
| TW | 200735709 | 9/2007 |
| TW | I298720 | 7/2008 |
| TW | 201006908 | 2/2010 |
| WO | WO 1998/055561 A1 | 12/1998 |
| WO | WO 2000/016593 A1 | 3/2000 |
| WO | WO 2000/018851 A1 | 4/2000 |
| WO | WO 2000/057676 A1 | 9/2000 |
| WO | WO 2000/070655 A2 | 11/2000 |
| WO | WO 2001/041512 A1 | 6/2001 |
| WO | WO 2006/033538 A1 | 3/2006 |
| WO | WO 2007/063796 A1 | 6/2007 |
| WO | WO 2009/075741 A1 | 6/2009 |
| WO | WO 2009/136595 A1 | 11/2009 |
| WO | WO 2010/137509 A1 | 12/2010 |
| WO | WO 2011/027653 A1 | 3/2011 |

OTHER PUBLICATIONS

Written Opinion re Application No. PCT/JP2013/075397, dated Dec. 10, 2013.

Chinese Office Action re Application No. CN 201380048942.0, dated Jun. 3, 2016.

* cited by examiner

LIGHT-EMITTING ELEMENT, LIGHT-EMITTING DEVICE, ELECTRONIC DEVICE, AND LIGHTING DEVICE

This application is a continuation of copending U.S. application Ser. No. 14/029,208, filed on Sep. 17, 2013 which is incorporated herein by reference.

TECHNICAL FIELD

One embodiment of the present invention relates to a light-emitting element in which an organic compound capable of providing light emission by application of an electric field is provided between a pair of electrodes, and also relates to a light-emitting device, an electronic device, and a lighting device including such a light-emitting element.

BACKGROUND ART

A light-emitting element using an organic compound as a luminous body, which has features such as thinness, lightness, high-speed response, and DC drive at low voltage, is expected to be applied to a next-generation flat panel display. In particular, a display device in which light-emitting elements are arranged in matrix is considered to have advantages in a wide viewing angle and excellent visibility over a conventional liquid crystal display device.

A light-emitting element is said to have the following light emission mechanism: when voltage is applied between a pair of electrodes with an EL layer including a light-emitting substance provided therebetween, electrons injected from the cathode and holes injected from the anode are excited in a light emission center of the EL layer, and energy is released and light is emitted when the excited state returns to a ground state. The excited states generated in the case of using an organic compound as a light-emitting substance are a singlet excited state and a triplet excited state. Luminescence from the singlet excited state (S1) is referred to as fluorescence, and luminescence from the triplet excited state (T1) is referred to as phosphorescence. The statistical generation ratio of the excited states in the light-emitting element is considered to be $S_1:T_1=1:3$.

Therefore, the EL layer of the light-emitting element includes a host material and a guest material (a phosphorescent compound), whereby the light-emitting element can have an element structure that utilizes phosphorescence as well as fluorescence and element characteristics can be improved (e.g., see Patent Document 1).

Further, the EL layer includes a hole-injection layer, a hole-transport layer, a light-emitting layer, an electron-transport layer, an electron-injection layer, or the like, and includes at least a light-emitting layer. Note that materials suitable for respective functions of these layers have been developed to be applied, whereby element characteristics are improved (e.g., see Patent Document 2).

REFERENCE

[Patent Document 1]
[Patent Document 1] Japanese Published Patent Application No. 2010-182699

[Patent Document 2] Japanese Published Patent Application No. 2001-261680

DISCLOSURE OF INVENTION

In order to improve element characteristics of a light-emitting element, it is very important to increase a property of injecting carriers to a light-emitting layer because emission efficiency can be increased. Note that in the case where the light-emitting layer includes a host material and a guest material, a magnitude relation of the highest occupied molecular orbital level (hereinafter referred to as a HOMO level) of the host material and the HOMO level of the guest material is considered to affect a property of injecting carriers (holes) to the light-emitting layer. This is considered to be because in the case where the HOMO level of the host material is significantly lower than the HOMO level of the guest material, holes are selectively trapped at an interface on the anode side of the light-emitting layer by the guest material and thus holes are less likely to be distributed in the whole light-emitting layer. Therefore, it is preferable that the difference between the HOMO level of the host material used for the light-emitting layer and the HOMO level of the guest material which is used together with the host material be small and the host material used for the light-emitting layer have a high triplet excited energy level (T1 level). By such a combination of the host material and the guest material, carrier balance in a light-emitting layer is favorable; thus, a light-emitting element having high emission efficiency is provided.

In the case where the guest material used for the light-emitting layer has a high HOMO level, the host material which is used together with the guest material preferably has a high HOMO level in accordance with it. However, in the case of the guest material emitting phosphorescence with a short wavelength, such as blue light, when the HOMO level is high, the T1 level becomes high in accordance with it. Therefore, the use of the material satisfying such both conditions is considered to be effective to improve emission efficiency. In view of the above, the host material that can widely select a phosphorescent compound which is the guest material even if the host material has a higher HOMO level and a higher T1 level than a conventional host material was calculated by quantum chemical calculation and an examination of a molecular structure of the host material suitable for the light-emitting layer of the light-emitting element emitting phosphorescence was conducted.

In the design of the molecular structure, the HOMO level can be increased by an increase in electron density in molecules. However, when an amine structure or the like is introduced so that the electron density is increased, conjugation extends in molecules and thus the T1 level is likely to be reduced. In view of the above, the electron density is increased by introduction of another 5-membered ring in molecules, whereby the T1 level is kept high while the HOMO level is kept high.

Accordingly, it was found that an optimal structure of the host material used for the light-emitting layer of the light-emitting element emitting phosphorescence is a substance containing a 5-membered ring shown by the following general formula (G1), in which a plurality of 5-membered rings is introduced in molecules in order to increase electron density, which leads to an increase in the HOMO level, and T1 level.

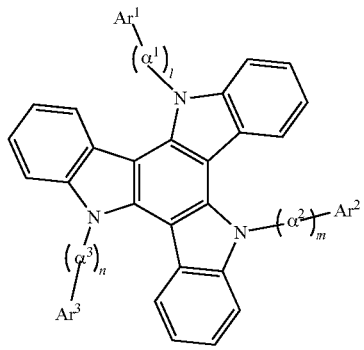

(G1)

(In the formula, $\alpha^1$ to $\alpha^3$ separately represent a substituted or unsubstituted phenylene group or a substituted or unsubstituted biphenyldiyl group, $Ar^1$ to $Ar^3$ separately represent any of a substituted or unsubstituted phenyl group, a substituted or unsubstituted pyridyl group, a substituted or unsubstituted pyrimidyl group, a substituted or unsubstituted naphthyl group, a substituted or unsubstituted fluorenyl group, a substituted or unsubstituted triphenylenyl group, and a substituted or unsubstituted phenanthrenyl group, and l, m and n separately are 0 or 1.)

That is, in one embodiment of the present invention, a light-emitting layer of a light-emitting element includes a first organic compound which is a host material and a second organic compound which is a guest material, and the difference between the HOMO level of the first organic compound and the HOMO level of the second organic compound is lower than or equal to 0.3 eV.

Further, in one embodiment of the present invention, a light-emitting element includes a layer including a first organic compound represented by the above general formula (G1) and a second organic compound which is a guest material between a pair of electrodes. Note that in the above structure, the difference between the HOMO level of the first organic compound and the HOMO level of the second organic compound is lower than or equal to 0.3 eV.

Further, in the above structure, it is preferable that the second organic compound be a phosphorescent compound (an organometallic complex or the like), particularly, a material having a HOMO level higher than or equal to −5.8 eV.

In each of the above structures, a structure including a hole-injection layer, a hole-transport layer, an electron-injection layer, or an electron-transport layer in addition to the light-emitting layer including the first organic compound and the second organic compound can be employed. At that case, the first organic compound represented by the above general formula (G1) is a compound having a donor property; therefore, the first organic compound can be used for the hole-injection layer or the hole-transport layer.

Further, in each of the above structures, as the first organic compound represented by the above general formula (G1), particularly, an organic compound represented by the following structural formula (100) (10,15-dihydro-5,10,15-triphenyl-5H-diindolo[3,2-a:3',2'-c]carbazole (abbreviation: P3Dic)) can be used.

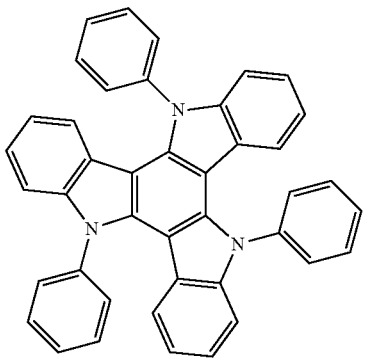

(100)

Other embodiments of the present invention are not only a light-emitting device including the light-emitting element but also an electronic device and a lighting device each including the light-emitting device. The light-emitting device in this specification refers to an image display device and a light source (e.g., a lighting device). In addition, the light-emitting device includes all the following modules: a module in which a connector, such as a flexible printed circuit (FPC) or a tape carrier package (TCP), is attached to a light-emitting device; a module in which a printed wiring board is provided at the end of a TCP; and a module in which an integrated circuit (IC) is directly mounted on a light-emitting element by a chip-on-glass (COG) method.

In one embodiment of the present invention, the difference between the HOMO level of a host material included in a light-emitting layer of a light-emitting element emitting phosphorescence and the HOMO level of a guest material can be lower than or equal to 0.3 eV; therefore, the light-emitting element having high emission efficiency can be realized.

BEST MODE FOR CARRYING OUT THE INVENTION

Hereinafter, embodiments of the present invention will be described in detail with reference to the drawings. Note that the present invention is not limited to the following description, and various changes and modifications can be made without departing from the spirit and scope of the present invention. Therefore, the present invention should not be construed as being limited to the description in the following embodiments.

Embodiment 1

In this embodiment, a light-emitting element emitting phosphorescence, which is one embodiment of the present invention, will be described.

Figure 1:
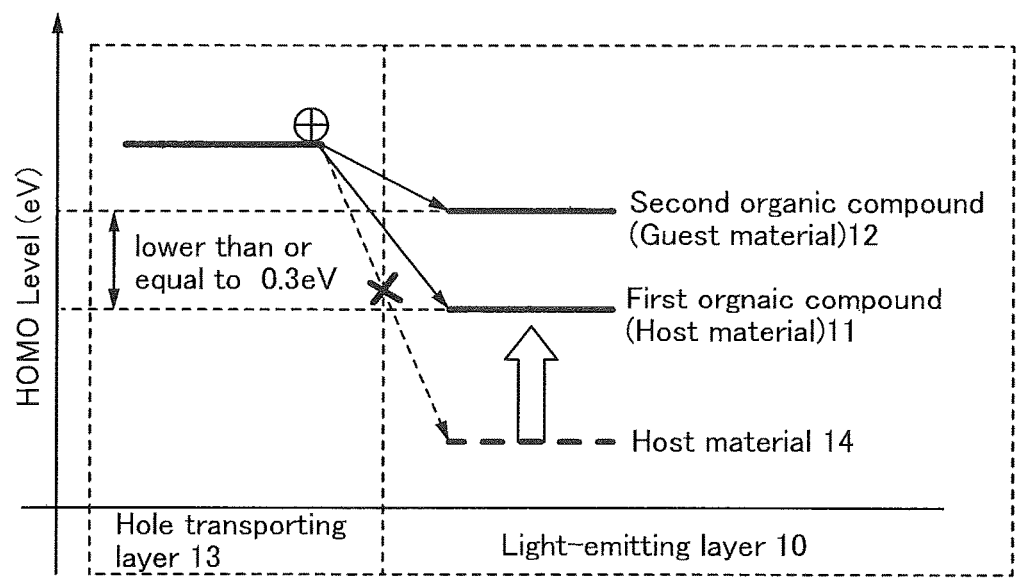
FIG. 1 illustrates a concept of one embodiment of the present invention.

The light-emitting element described in this embodiment includes, as illustrated in FIG. 1, a first organic compound (a host material) 11 and a second organic compound (a guest material) 12 in a light-emitting layer 10; the difference between the HOMO level of the first organic compound (the host material) 11 and the HOMO level of the second organic compound (the guest material) 12 is lower than or equal to 0.3 eV.

Note that, in injection of holes from a hole-transport layer 13 to the light-emitting layer 10, in the case where a host material 14 is used instead of the first organic compound (the host material) 11 in the light-emitting layer 10, even if the holes are injected from the hole-transport layer 13 to the host material 14, most of the holes are likely to enter the level of the second organic compound (the guest material) 12 in the vicinity of an interface between the hole-transport layer 13 and the light-emitting layer 10 immediately; therefore, a property of injecting or transporting holes to the light-emitting layer 10 is decreased. Thus, it is considered that the driving voltage is likely to be increased. However, as the host material in the light-emitting layer 10, in the case where the first organic compound (the host material) 11 having a higher HOMO level than the host material 14 (that is, the difference between the HOMO level of the second organic compound (the guest material) 12 and the HOMO level of the first organic compound 11 is small, preferably, lower than or equal to 0.3 eV) is used, holes are likely to enter both of the level of the first organic compound (the host material) 11 and the level of the second organic compound (the guest material) 12; therefore, a property of injecting or transporting holes to the light-emitting layer 10 of the light-emitting element can be increased.

Here, as a result of calculation of a host material having a higher HOMO level and a higher T1 level than the host material 14 by quantum chemical calculation, it was found that as an optimal structure of the first organic compound (the host material) 11, a substance containing a 5-membered ring shown by the following general formula (G1), in which a plurality of 5-membered rings is introduced in order to increase electron density, which leads to an increase in the HOMO level, and T1 level which is decreased due to introduction of nitrogen, is preferably used.

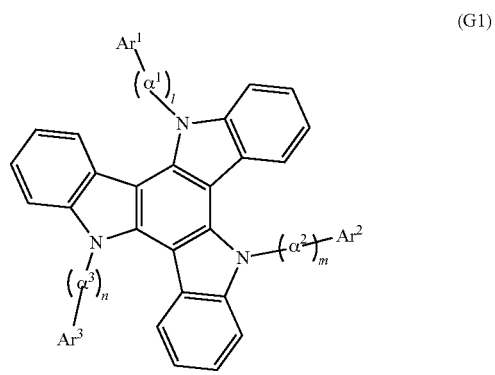

(G1)

(In the formula, $\alpha^1$ to $\alpha^3$ separately represent a substituted or unsubstituted phenylene group or a substituted or unsubstituted biphenyldiyl group, $Ar^1$ to $Ar^3$ separately represent any of a substituted or unsubstituted phenyl group, a substituted or unsubstituted pyridyl group, a substituted or unsubstituted pyrimidyl group, a substituted or unsubstituted naphthyl group, a substituted or unsubstituted fluorenyl group, a substituted or unsubstituted triphenylenyl group, and a substituted or unsubstituted phenanthrenyl group, and l, m and n separately are 0 or 1.)

In view of the above, the light-emitting element emitting phosphorescence described in this embodiment includes the first organic compound (the host material) shown by the above general formula (G1) and the second organic compound (the guest material) in the light-emitting layer; the difference between the HOMO level of the first organic compound (the host material) and the HOMO level of the second organic compound (the guest material) is lower than or equal to 0.3 eV.

Next, the light-emitting element which is one embodiment of the present invention will be described with reference to FIG. 2.

Figure 2:
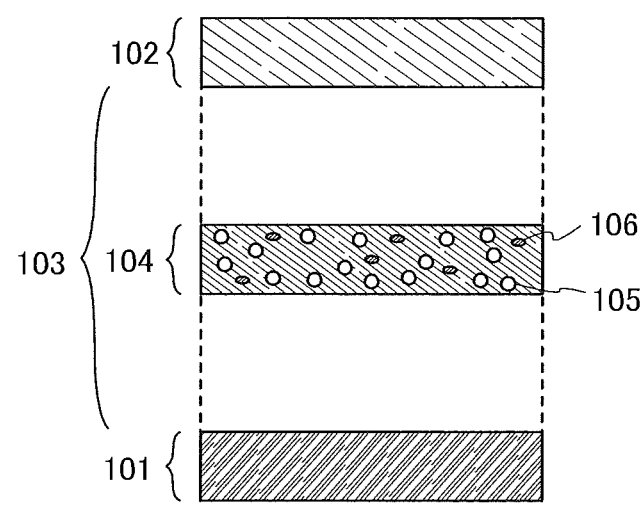
FIG. 2 illustrates a structure of a light-emitting element.

The light-emitting element which is one embodiment of the present invention has a structure in which, as illustrated in FIG. 2, a light-emitting layer 104 including a first organic compound (a host material) 105 shown by the above general formula (G1) and a second organic compound (a guest material) 106 which is a phosphorescent compound is interposed between a pair of electrodes (an anode 101 and a cathode 102). Note that the light-emitting layer 104 is one of functional layers included in an EL layer 103 which is in contact with the pair of electrodes. The EL layer 103 can include not only the light-emitting layer 104 but also an appropriately selected layer in a desired position, such as a hole-injection layer, a hole-transport layer, an electron-transport layer, or an electron-injection layer.

Note that specific examples of the first organic compound (the host material) 105 shown by the above general formula (G1) include the following substances.

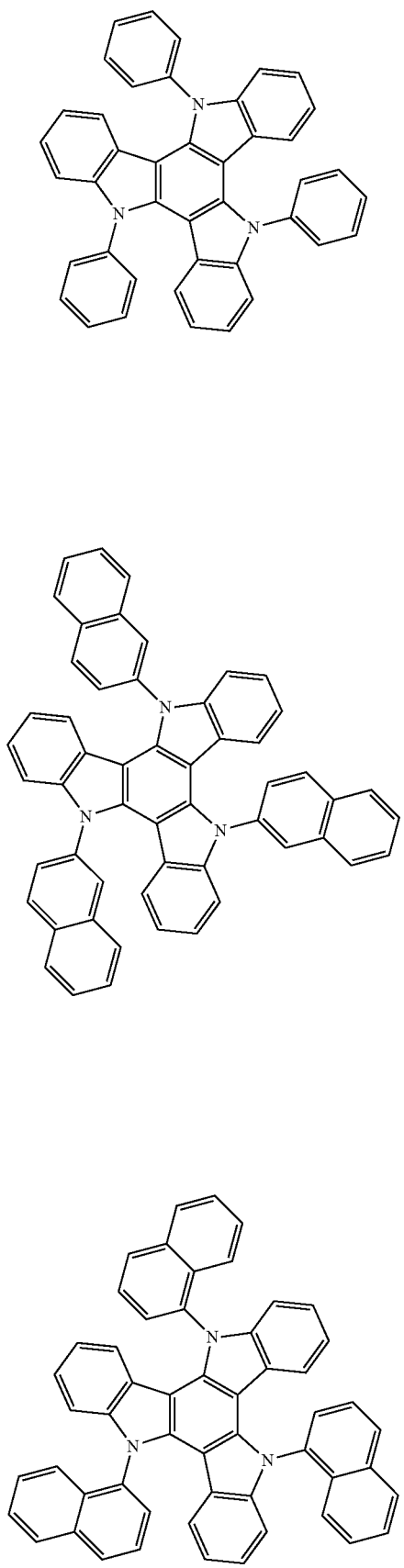
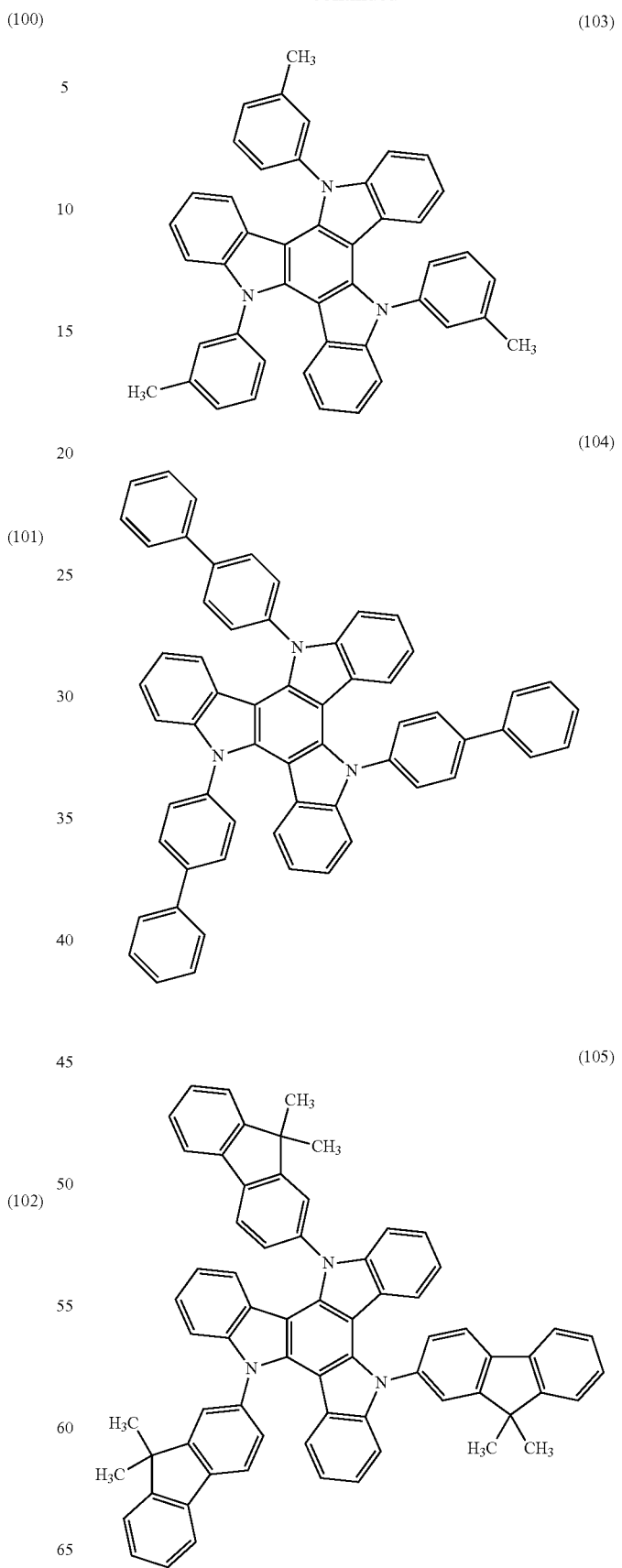

-continued

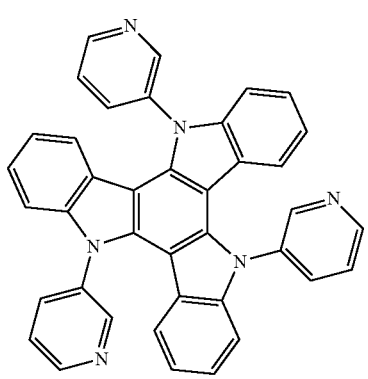
(106)

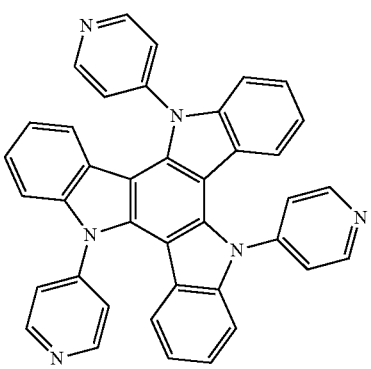
(107)

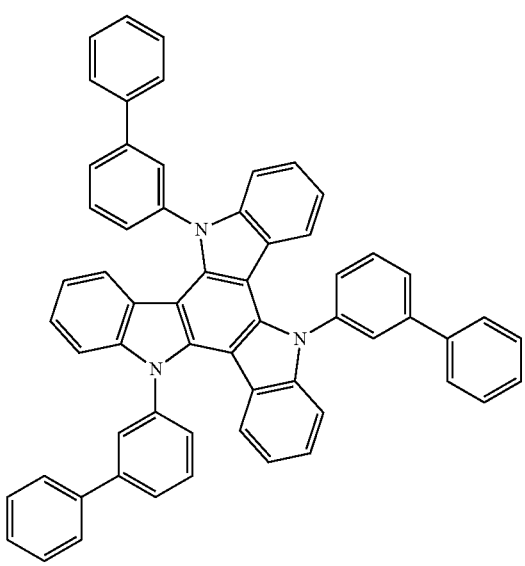
(108)

In addition, it is preferable that the second organic compound (the guest material) 106 be a phosphorescent compound (an organometallic complex or the like), particularly, a material having a HOMO level higher than or equal to −5.8 eV.

Note that examples of an organometallic complex which is a phosphorescent compound include tris(2-phenylpyridinato)iridium(III) (abbreviation: Ir(ppy)$_3$); bis(2-phenylpyridinato)iridium(III) acetylacetonate (abbreviation: Ir(ppy)$_2$(acac)); bis(2-phenylbenzothiazolato-N,C$^{2'}$)iridium (III) acetylacetonate (abbreviation: Ir(bt)$_2$(acac)); bis[2-(2'-benzo[4,5-α]thienyl)pyridinato-N,C$^{3'}$]iridium(III) acetylacetonate (abbreviation: Ir(btp)$_2$(acac)); (acetylacetonato)bis [2,3-bis(4-fluorophenyl)quinoxalinato]iridium(III) (abbreviation: Ir(Fdpq)$_2$(acac)); (acetylacetonato)bis(2,3,5-triphenylpyrazinato)iridium (III) (abbreviation: Ir(tppr)$_2$ (acac)); 2,3,7,8,12,13,17,18-octaethyl-21H,23H-porphyrin platinum(II) (abbreviation: PtOEP); (acetylacetonato)bis(6-tert-butyl-4-phenylpyrimidinato)iridium(III) (another name: bis[2-(6-tert-butyl-4-pyrimidinyl-κN3)phenyl-κC] (2,4-pentanedionato-κ$^2$O,O')iridium(III) (abbreviation: [Ir(tBuppm)$_2$(acac)]); bis(3,5-dimethyl-2-phenylpyrazinato) (dipivaloylmethanato)iridium(III) (abbreviation: [Ir(mppr-Me)$_2$(dpm)]); and (acetylacetonato)bis(6-methyl-4-phenylpyrimidinato)iridium(III) (another name: bis[2-(6-methyl-4-pyrimidinyl-κN3)phenyl-κC](2,4-pentanedionato-κ$^2$O,O')iridium(III) (abbreviation: [Ir(mppm)$_2$(acac)]).

The first organic compound 105 and the second organic compound 106 are not limited to the above substances as long as the difference between the HOMO level of the first organic compound 105 and the HOMO level of the second organic compound 106 is lower than or equal to 0.3 eV.

In the light-emitting element in this embodiment which is one embodiment of the present invention, the difference between the HOMO level of a host material included in the light-emitting layer of the light-emitting element emitting phosphorescence and the HOMO level of a guest material can be lower than or equal to 0.3 eV; therefore, the light-emitting element having high emission efficiency can be realized by an increase in the property of injecting holes to the light-emitting layer.

Embodiment 2

In this embodiment, a structure of a light-emitting element which is one embodiment of the present invention and a manufacturing method thereof are described with reference to FIG. 3.

Figure 3:
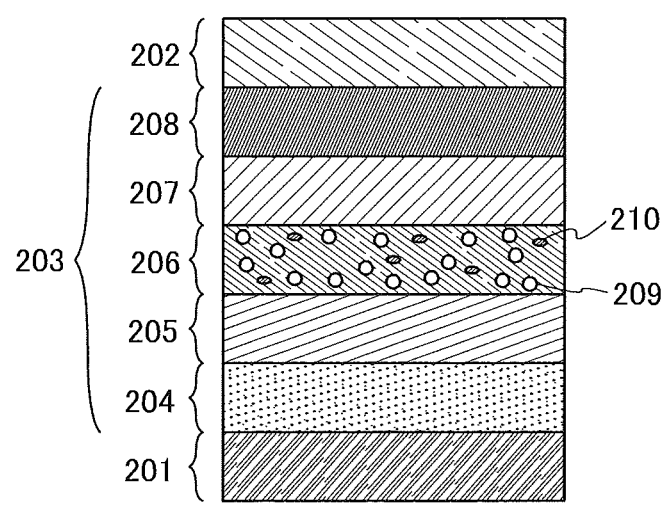
FIG. 3 illustrates a structure of a light-emitting element.

In a light-emitting element described in this embodiment, as illustrated in FIG. 3, an EL layer 203 including a light-emitting layer 206 is provided between a pair of electrodes (a first electrode (anode) 201 and a second electrode (cathode) 202), and the EL layer 203 includes a hole-injection layer 204, a hole-transport layer 205, an electron-transport layer 207, an electron-injection layer 208, and the like in addition to the light-emitting layer 206.

The light-emitting layer 206 includes a first organic compound 209 represented by the following general formula (G1) and a second organic compound 210, as in the light-emitting element described in Embodiment 1. Further, the difference between the HOMO level of the first organic compound (the host material) 209 and the HOMO level of the second organic compound (the guest material) 210 is lower than or equal to 0.3 eV.

Note that, with the structure of the light-emitting layer of the light-emitting element as described above, a property of injecting holes from a hole-transport layer to the light-emitting layer can be increased, so that emission efficiency of the light-emitting element can be increased.

Note that the same substances as those in Embodiment 1 can be used as the first organic compound 209 represented by the following general formula (G1) and the second organic compound 210 in the above structure, and thus description of specific examples thereof is omitted.

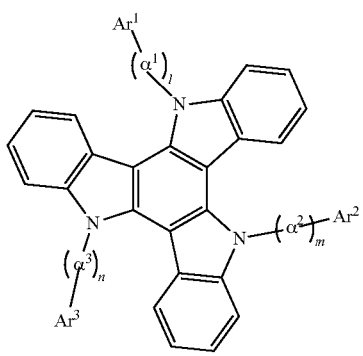

(G1)

(In the formula, $\alpha^1$ to $\alpha^3$ separately represent a substituted or unsubstituted phenylene group or a substituted or unsubstituted biphenyldiyl group, $Ar^1$ to $Ar^3$ separately represent any of a substituted or unsubstituted phenyl group, a substituted or unsubstituted pyridyl group, a substituted or unsubstituted pyrimidyl group, a substituted or unsubstituted naphthyl group, a substituted or unsubstituted fluorenyl group, a substituted or unsubstituted triphenylenyl group, and a substituted or unsubstituted phenanthrenyl group, and l, m and n separately are 0 or 1.)

The skeleton shown by the above general formula (G1) (the diindolocarbazole skeleton) is a skeleton that is highly planar and has a high carrier-transport property. In particular, the skeleton has a high HOMO level and a high hole-transport property.

Note that in the case where $\alpha^1$ to $\alpha^3$ and $Ar^1$ to $Ar^3$ have a substituent in the above general formula (G1), an alkyl group having 1 to 6 carbon atoms is preferable.

Further, in the above general formula (G1), even when $\alpha^1$ to $\alpha^3$ and $Ar^1$ to $Ar^3$ are bonded to the diindolocarbazole skeleton, electron density is less likely to extend from the diindolocarbazole skeleton to these substituents; therefore, the structure is preferable in that the T1 level is not reduced but is maintained.

Furthermore, in the above general formula (G1), it is preferable that $Ar^1$ to $Ar^3$ separately represent any of a substituted or unsubstituted pyridyl group and a substituted or unsubstituted pyrimidyl group, in which case the substance itself has a bipolar property. In addition, here, it is preferable that l, m, and n be 1 because HOMO-LUMO overlap can be reduced by the diindolocarbazole skeleton and $Ar^1$ to $Ar^3$; therefore, the T1 can be kept high.

Further, in the above general formula (G1), it is preferable that $\alpha^1$ to $\alpha^3$ separately represent any of a substituted or unsubstituted phenylene group and a substituted or unsubstituted biphenyldiyl group, $Ar^1$ to $Ar^3$ separately represent any of a substituted or unsubstituted phenyl group, a substituted or unsubstituted pyridyl group, and a substituted or unsubstituted pyrimidyl group, and l, m and n be 0 or 1, in which case the T1 can be kept high. This is because in the case where $\alpha^1$ to $\alpha^3$ are each composed of a six-membered ring, the T1 can be kept higher than in the case where a higher condensed ring is used.

Further, in the above general formula (G1), it is preferable that $\alpha^1$ to $\alpha^3$ separately represent any of a substituted or unsubstituted phenylene group and a substituted or unsubstituted biphenyldiyl group, $Ar^1$ to $Ar^3$ separately represent any of a substituted or unsubstituted phenyl group, a substituted or unsubstituted naphthyl group, a substituted or unsubstituted fluorenyl group, a substituted or unsubstituted triphenylenyl group, and a substituted or unsubstituted phenanthrenyl group, in which case such a group is a hydrocarbon group; therefore, the HOMO level can be kept high.

Next, a manufacturing method of the light-emitting element described in this embodiment is specifically described.

For the first electrode (anode) 201 and the second electrode (cathode) 202, a metal, an alloy, an electrically conductive compound, a mixture thereof, or the like can be used. Specific examples are indium oxide-tin oxide (indium tin oxide (ITO)), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti). Other examples are elements that belong to Group 1 or 2 in the periodic table, for example, an alkali metal such as lithium (Li) or cesium (Cs), an alkaline earth metal such as calcium (Ca) or strontium (Sr), magnesium (Mg), an alloy containing such an element (MgAg or AlLi), a rare earth metal such as europium (Eu) or ytterbium (Yb), an alloy containing such an element, and graphene. The first electrode (anode) 201 and the second electrode (cathode) 202 can be formed by, for example, a sputtering method, an evaporation method (including a vacuum evaporation method), or the like.

Examples of a substance having a high hole-transport property which is used for the hole-injection layer 204 and the hole-transport layer 205 include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB), 3-[N-(9-phenylcarbazol-3-yl)-N-phenylamino]-9-phenyl-carbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1). Alternatively, the following carbazole derivative can be used: 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-Carbazole (abbreviation: CzPA). The substances mentioned here are mainly ones that have a hole mobility of $10^{-6}$ cm$^2$/Vs or higher. However, other substances than the above described materials may also be used as long as the substances have higher hole-transport properties than electron-transport properties.

Further, a polymer such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can be used.

Note that the first organic compound represented by the general formula (G1) is a substance having a high donor property and a high hole-transport property; therefore, the first organic compound can be also used for the hole-injection layer and the hole-transport layer.

Further, examples of an acceptor substance which can be used for the hole-injection layer 204 include oxides of transition metals, oxides of metals belonging to Groups 4 to 8 of the periodic table, and the like. Specifically, molybdenum oxide is particularly preferable.

The light-emitting layer 206 includes the first organic compound represented by the general formula (G1) and the second organic compound, as described above.

The electron-transport layer 207 is a layer that contains a substance having a high electron-transport property. For the electron-transport layer 207, it is possible to use a metal complex such as Alq$_3$, tris(4-methyl-8-quinolinolato)aluminum(III) (abbreviation: Almq$_3$), bis(10-hydroxybenzo[h]quinolinato)beryllium(II) (abbreviation: BeBq$_2$), BAlq, Zn(BOX)$_2$, or bis[2-(2-hydroxyphenyl)benzothiazolato]zinc (II) (abbreviation: Zn(BTZ)$_2$). Further, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4'-tert-butylphenyl)-4-phenyl-5-(4''-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can also be used. Further, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can be used. The substances mentioned here are mainly ones that have an electron mobility of $10^{-6}$ cm$^2$/Vs or higher. However, substances other than the above described substances may also be used in the electron-transport layer 207 as long as the substances have higher electron-transport properties than hole-transport properties.

The electron-transport layer 207 is not limited to a single layer, and may be a stack of two or more layers containing any of the above substances.

The electron-injection layer 208 is a layer that contains a substance having a high electron-injection property. For the electron-injection layer 208, an alkali metal, an alkaline earth metal, or a compound thereof, such as lithium fluoride (LiF), cesium fluoride (CsF), calcium fluoride (CaF$_2$), or lithium oxide (LiO$_x$), can be used. Alternatively, a rare earth metal compound like erbium fluoride (ErF$_3$) can be used. The above-mentioned substances for forming the electron-transport layer 207 can also be used.

Alternatively, a composite material in which an organic compound and an electron donor (a donor) are mixed may be used for the electron-injection layer 208. The composite material is superior in an electron-injection property and an electron-transport property, since electrons are generated in the organic compound by the electron donor. The organic compound here is preferably a material excellent in transporting the generated electrons, and specifically any of the above substances (such as metal complexes and heteroaromatic compounds) for the electron-transport layer 207 can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given. Further, an alkali metal oxide or an alkaline earth metal oxide is preferable, and for example, lithium oxide, calcium oxide, barium oxide, and the like can be given. Alternatively, Lewis base such as magnesium oxide can also be used. An organic compound such as tetrathiafulvalene (abbreviation: TTF) can also be used.

Note that the hole-injection layer 204, the hole-transport layer 205, the light-emitting layer 206, the electron-transport layer 207, and the electron-injection layer 208 which are mentioned above can each be formed by a method such as an evaporation method (including a vacuum evaporation method), an inkjet method, or a coating method.

Light emission obtained in the light-emitting layer 206 of the above-described light-emitting element is extracted to the outside through either the first electrode 201 or the second electrode 202 or both. Therefore, either the first electrode 201 or the second electrode 202 in this embodiment, or both, is an electrode having a light-transmitting property.

In the light-emitting element described in this embodiment, the light-emitting layer includes the first organic compound represented by the above general formula (G1) and the second organic compound, and the difference between the HOMO level of the first organic compound (the host material) and the HOMO level of the second organic compound (the guest material) is lower than or equal to 0.3 eV. Therefore, the light-emitting element having high emission efficiency can be achieved.

Note that the light-emitting element described in this embodiment is one embodiment of the present invention and is particularly characterized by the structure of the light-emitting layer. Therefore, when the structure described in this embodiment is employed, a passive matrix light-emitting device, an active matrix light-emitting device, and the like can be manufactured. Each of these light-emitting devices is included in the present invention.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed using both of an n-type TFT and a p-type TFT or only either an n-type TFT or a p-type TFT. Furthermore, there is no particular limitation on the crystallinity of a semiconductor film used for the TFT. For example, an amorphous semiconductor film, a crystalline semiconductor film, an oxide semiconductor film, or the like can be used.

Note that the structure described in this embodiment can be used in combination with any of the structures described in the other embodiments, as appropriate.

Embodiment 3

In this embodiment, as one embodiment of the present invention, a light-emitting element (hereinafter referred to as tandem light-emitting element) in which a plurality of EL layers are included so as to sandwich a charge-generation layer will be described.

Figure 4A:
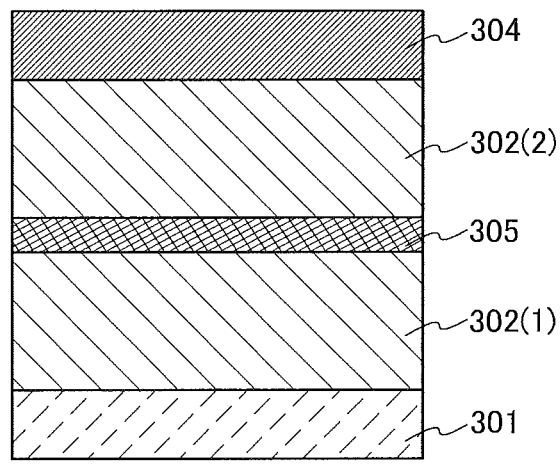
FIGS. 4A and 4B illustrate structures of light-emitting elements.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 4A.

In this embodiment, the first electrode 301 functions as an anode, and the second electrode 304 functions as a cathode. Note that the first electrode 301 and the second electrode 304 can have structures similar to those described in Embodiment 1. In addition, although the plurality of EL layers (the first EL layer 302(1) and the second EL layer 302(2)) may have structures similar to those described in Embodiment 1 or 2, any of the EL layers may have a structure similar to that described in Embodiment 1 or 2. In other words, the structures of the first EL layer 302(1) and the second EL layer 302(2) may be the same or different from each other and can be similar to those described in Embodiment 1 or 2.

Further, a charge-generation layer 305 is provided between the plurality of EL layers (the first EL layer 302(1) and the second EL layer 302(2)). The charge generation layer 305 has a function of injecting electrons into one of the EL layers and injecting holes into the other of the EL layers when a voltage is applied to the first electrode 301 and the second electrode 304. In this embodiment, when voltage is applied such that the potential of the first electrode 301 is higher than that of the second electrode 304, the charge-generation layer 305 injects electrons into the first EL layer 302(1) and injects holes into the second EL layer 302(2).

Note that in terms of light extraction efficiency, the charge-generation layer 305 preferably has a light-transmitting property with respect to visible light (specifically, the charge-generation layer 305 has a visible light transmittance of 40% or more). Further, the charge generation layer 305 functions even if it has lower conductivity than the first electrode 301 or the second electrode 304.

The charge generation layer 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^{-6}$ cm$^2$/Vs or higher. However, substances other than the above substances may be used as long as they are organic compounds having a hole-transport property higher than an electron-transport property.

Further, as the electron acceptor, 7,7,8,8-tetracyano-2,3,5,6-tetrafluoroquinodimethane (abbreviation: $F_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable since it is stable in the air and its hygroscopic property is low and is easily treated.

On the other hand, in the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, BPhen, BCP, or the like can be used. The substances mentioned here are mainly ones that have an electron mobility of $10^{-6}$ cm$^2$/Vs or higher. Note that substances other than the above substances may be used as long as they are organic compounds having an electron-transport property higher than a hole-transport property.

As the electron donor, it is possible to use an alkali metal, an alkaline earth metal, a rare earth metal, a metal belonging to Group 2 or 13 of the periodic table, or an oxide or a carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge generation layer 305 by using the above materials can suppress an increase in driving voltage caused by the stack of the EL layers.

Figure 4B:
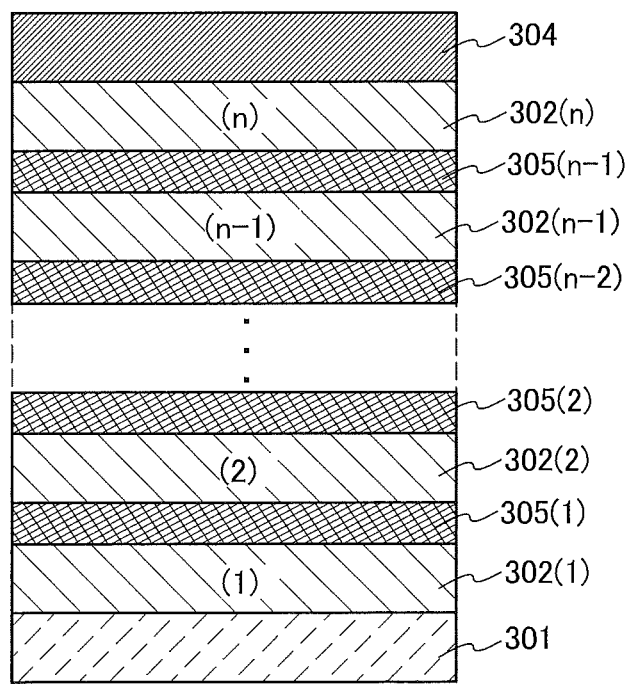

Although the light-emitting element including two EL layers is described in this embodiment, the present invention can be similarly applied to a light-emitting element in which n EL layers (302(1) to 302(n)) (n is three or more) are stacked as illustrated in FIG. 4B. In the case where a plurality of EL layers are included between a pair of electrodes as in the light-emitting element according to this embodiment, charge generation layers (305(1) to 305(n−1)) are each provided between the EL layers, whereby light emission in a high luminance region can be obtained while current density is kept low; thus, a light-emitting element having a long lifetime can be obtained. When the light-emitting element is applied for illumination, voltage drop due to resistance of an electrode material can be reduced, thereby achieving homogeneous light emission in a large area. Moreover, a light-emitting device of low power consumption, which can be driven at low voltage, can be achieved.

Further, by forming EL layers to emit light of different colors from each other, a light-emitting element as a whole can provide light emission of a desired color. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. That is, white light emission can be obtained by mixture of light from substances, of which the light emission colors are complementary colors.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

In the structure described in this embodiment in which EL layers are stacked with a charge generation layer provided therebetween, by adjusting the distance between electrodes (the first electrode 301 and the second electrode 304), the light-emitting element can have a micro optical resonator (microcavity) structure utilizing a resonant effect of light.

Note that the structure described in this embodiment can be combined as appropriate with any of the structures described in the other embodiments.

Embodiment 4

In this embodiment, a light-emitting device including a light-emitting element which is one embodiment of the present invention will be described.

Note that any of the light-emitting elements described in the other embodiments can be applied to the light-emitting element. The light-emitting device can be either a passive matrix light-emitting device or an active matrix light-emitting device. In this embodiment, an active matrix light-emitting device is described with reference to FIGS. 5A and 5B.

Figure 5A:
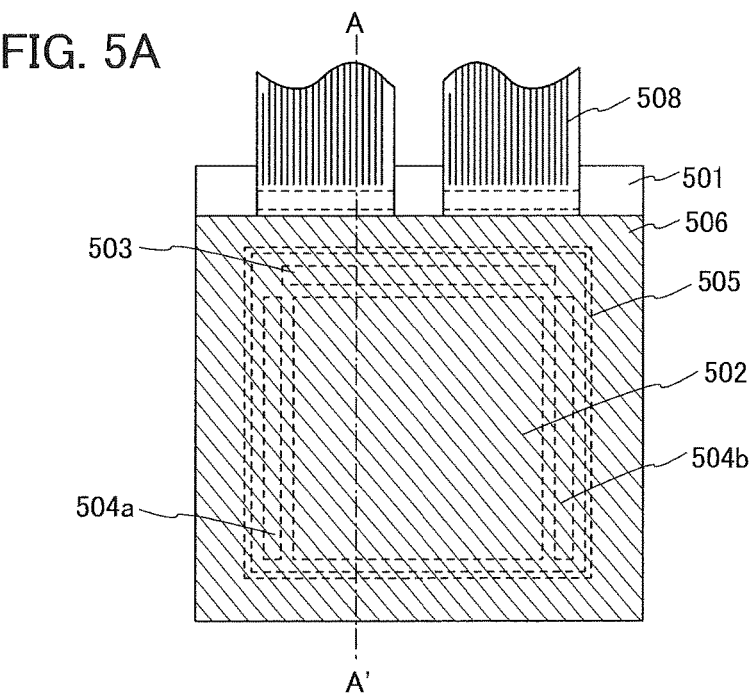
FIGS. 5A and 5B illustrate a light-emitting device.
Figure 5B:
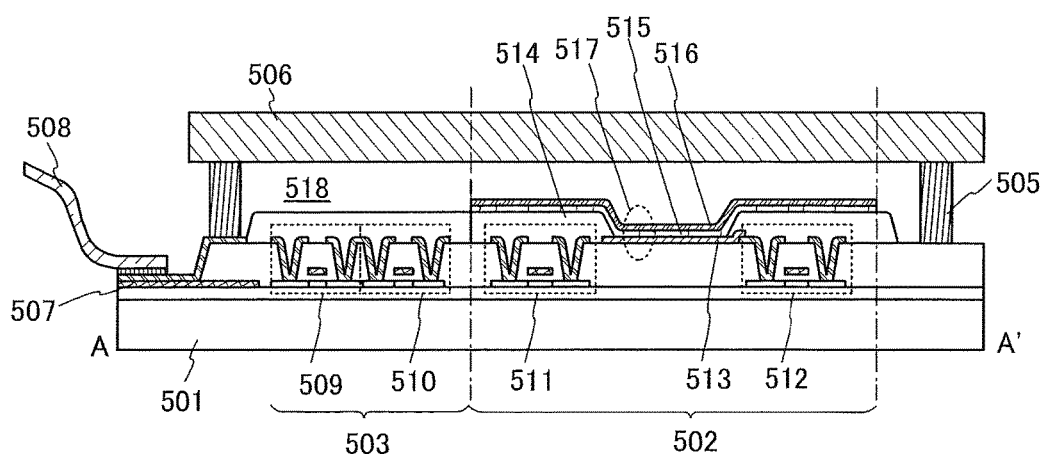

Note that FIG. 5A is a top view illustrating a light-emitting device and FIG. 5B is a cross-sectional view taken along chain line A-A' in FIG. 5A. The active matrix light-emitting device according to this embodiment includes a pixel portion 502 provided over an element substrate 501, a driver circuit portion (a source line driver circuit) 503, and driver circuit portions (gate line driver circuits) 504a and 504b. The pixel portion 502, the driver circuit portion 503, and the driver circuit portions 504a and 504b are sealed between the element substrate 501 and the sealing substrate 506 by a sealant 505.

In addition, there is provided a lead wiring 507 over the element substrate 501. The lead wiring 507 is provided for connecting an external input terminal through which a signal (e.g., a video signal, a clock signal, a start signal, and a reset signal) or a potential from the outside is transmitted to the driver circuit portion 503 and the driver circuit portions 504a and 504b. Here, an example is described in which a flexible printed circuit (FPC) 508 is provided as the external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is explained with reference to FIG. 5B. The driver circuit portion and the pixel portion are formed over the element substrate 501; here are illustrated the driver circuit portion 503 which is the source line driver circuit and the pixel portion 502.

An example is illustrated in which a CMOS circuit which is a combination of an n-channel TFT 509 and a p-channel TFT 510 is formed as the driver circuit portion 503. Note that a circuit included in the driver circuit portion may be formed using various CMOS circuits, PMOS circuits, or NMOS circuits. Although a driver integrated type in which the driver circuit is formed over the substrate is described in this embodiment, the driver circuit may not necessarily be formed over the substrate, and the driver circuit can be formed outside, not over the substrate.

The pixel portion 502 is formed of a plurality of pixels each of which includes a switching TFT 511, a current control TFT 512, and a first electrode (anode) 513 which is electrically connected to a wiring (a source electrode or a drain electrode) of the current control TFT 512. Note that an insulator 514 is formed to cover end portions of the first electrode (anode) 513. In this embodiment, the insulator 514 is formed using a positive photosensitive acrylic resin.

In addition, in order to obtain favorable coverage by a film which is to be stacked over the insulator 514, the insulator 514 is preferably formed so as to have a curved surface with curvature at an upper edge portion or a lower edge portion. For example, in the case of using a positive photosensitive acrylic resin as a material for the insulator 514, the insulator 514 is preferably formed so as to have a curved surface with a curvature radius (0.2 μm to 3 μm) at the upper edge portion. Note that the insulator 514 can be formed using either a negative photosensitive resin or a positive photosensitive resin. It is possible to use, without limitation to an organic compound, either an organic compound or an inorganic compound such as silicon oxide or silicon oxynitride.

A light-emitting element 517 is formed by stacking an EL layer 515 and a second electrode (cathode) 516 over the first electrode (anode) 513. The EL layer 515 includes at least the light-emitting layer described in Embodiment 1. Further, in the EL layer 515, a hole-injection layer, a hole-transport layer, an electron-transport layer, an electron-injection layer, a charge-generation layer, and the like can be provided as appropriate in addition to the light-emitting layer.

For the first electrode (anode) 513, the EL layer 515, and the second electrode (cathode) 516, the materials described in Embodiment 2 can be used. Although not illustrated, the second electrode (cathode) 516 is electrically connected to the FPC 508 which is the external input terminal.

In addition, although the cross-sectional view of FIG. 5B illustrates only one light-emitting element 517, a plurality of light-emitting elements are arranged in matrix in the pixel portion 502. Light-emitting elements that emit light of three kinds of colors (R, G, and B) are selectively formed in the pixel portion 502, whereby a light-emitting device capable of full color display can be obtained. Alternatively, a light-emitting device which is capable of full color display may be manufactured by a combination with color filters.

Further, the sealing substrate 506 is attached to the element substrate 501 with the sealant 505, whereby a light-emitting element 517 is provided in a space 518 surrounded by the element substrate 501, the sealing substrate 506, and the sealant 505. Note that the space 518 may be filled with an inert gas (such as nitrogen and argon) or the sealant 505.

An epoxy-based resin is preferably used for the sealant 505. A material used for these is desirably a material which does not transmit moisture or oxygen as possible. As the sealing substrate 506, a plastic substrate formed of fiberglass-reinforced plastics (FRP), polyvinyl fluoride (PVF), polyester, acrylic, or the like can be used besides a glass substrate or a quartz substrate.

As described above, an active matrix light-emitting device can be obtained.

Note that the structure described in this embodiment can be combined as appropriate with any of the structures described in the other embodiments.

Embodiment 5

In this embodiment, examples of a variety of electronic devices which are completed using a light-emitting device, which is fabricated using a light-emitting element of one embodiment of the present invention, are described with reference to FIGS. 6A to 6D and FIGS. 7A to 7C.

Examples of the electronic devices to which the light-emitting device is applied are a television device (also referred to as television or television receiver), a monitor of a computer or the like, a camera such as a digital camera or a digital video camera, a digital photo frame, a mobile phone (also referred to as cellular phone or cellular phone device), a portable game machine, a portable information terminal, an audio reproducing device, a large-sized game machine such as a pachinko machine, and the like. Specific examples of these electronic devices are shown in FIGS. 6A to 6D.

Figure 6A:
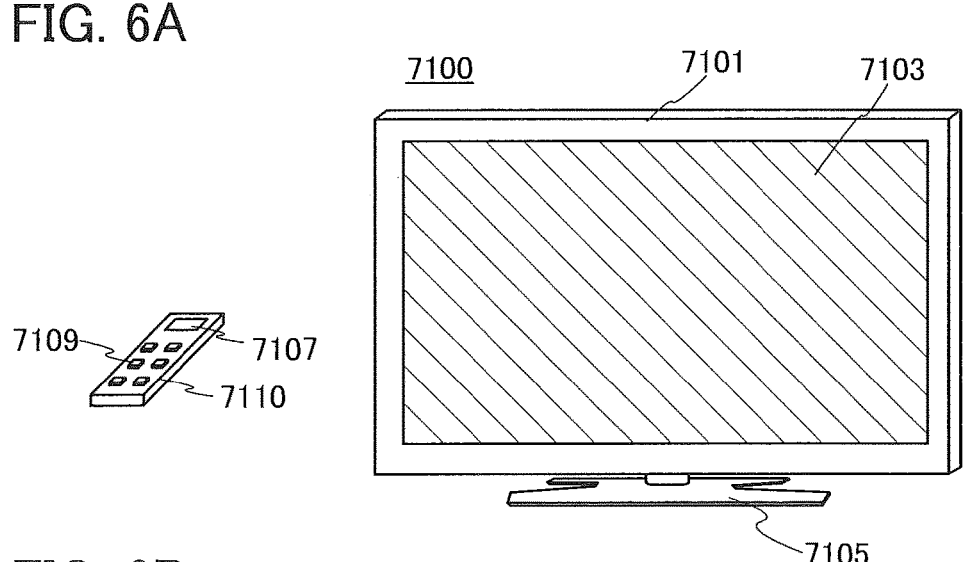
FIGS. 6A to 6D illustrate electronic devices.

FIG. 6A illustrates an example of a television device. In the television device 7100, a display portion 7103 is incorporated in a housing 7101. Images can be displayed by the display portion 7103, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, a general television broadcast can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 6B:
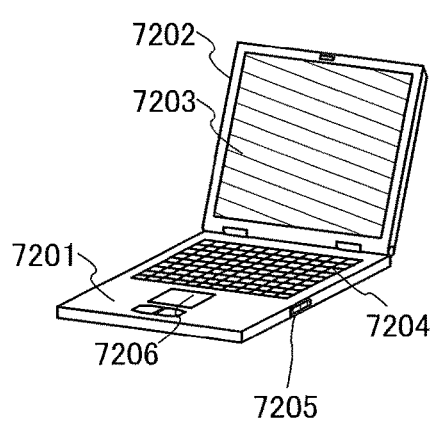

FIG. 6B illustrates a computer, which includes a main body 7201, a housing 7202, a display portion 7203, a keyboard 7204, an external connection port 7205, a pointing device 7206, and the like. Note that this computer is manufactured using the light-emitting device for the display portion 7203.

Figure 6C:
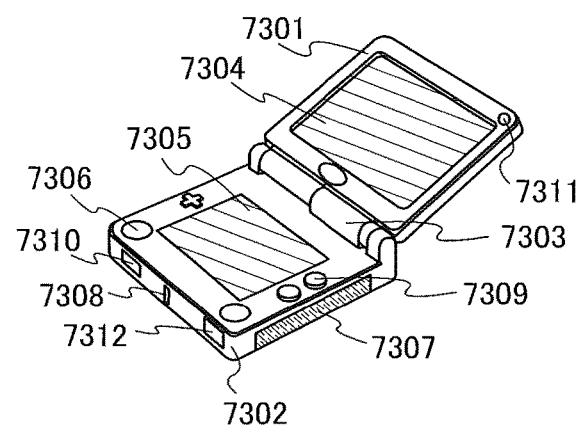

FIG. 6C illustrates a portable game machine having two housings, a housing 7301 and a housing 7302, which are connected with a joint portion 7303 so that the portable game machine can be opened or folded. A display portion 7304 is incorporated in the housing 7301 and a display portion 7305 is incorporated in the housing 7302. In addition, the portable game machine illustrated in FIG. 6C includes a speaker portion 7306, a recording medium insertion portion 7307, an LED lamp 7308, an input unit (an operation key 7309, a connection terminal 7310, a sensor 7311 (sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable game machine is not limited to the above as long as a light-emitting device is used for at least either the display portion 7304 or the display portion 7305, or both, and may include other accessories as appropriate. The portable game machine illustrated in FIG. 6C has a function of reading a program or data stored in a recording medium to display it in the display portion, and a function of sharing information with another portable game machine by wireless communication. Note that the functions of the portable game machine illustrated in FIG. 6C are not limited to these functions, and the portable game machine can have various functions.

Figure 6D:
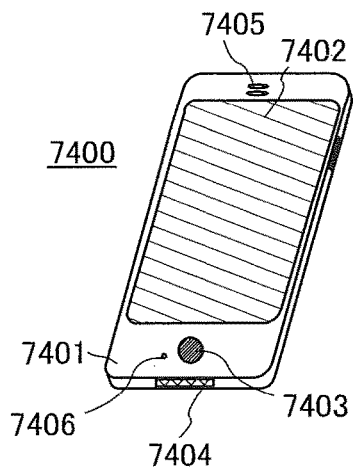

FIG. 6D illustrates an example of a mobile phone. The mobile phone 7400 is provided with a display portion 7402 incorporated in a housing 7401, operation buttons 7403, an external connection port 7404, a speaker 7405, a microphone 7406, and the like. Note that the mobile phone 7400 is manufactured using a light-emitting device for the display portion 7402.

When the display portion 7402 of the mobile phone 7400 illustrated in FIG. 6D is touched with a finger or the like, data can be input into the mobile phone 7400. Further, operations such as making a call and creating an e-mail can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or creating an e-mail, a text input mode mainly for inputting text is selected for the display portion 7402 so that text displayed on a screen can be inputted. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically changed by determining the orientation of the mobile phone 7400 (whether the mobile phone is placed horizontally or vertically for a landscape mode or a portrait mode).

The screen modes are switched by touching the display portion 7402 or operating the operation buttons 7403 of the housing 7401. Alternatively, the screen modes can be switched depending on kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken when the display portion 7402 is touched with the palm or the finger, whereby personal authentication can be performed. Further, by providing a backlight or a sensing light source which emits a near-infrared light in the display portion, an image of a finger vein, a palm vein, or the like can be taken.

Figure 7A:
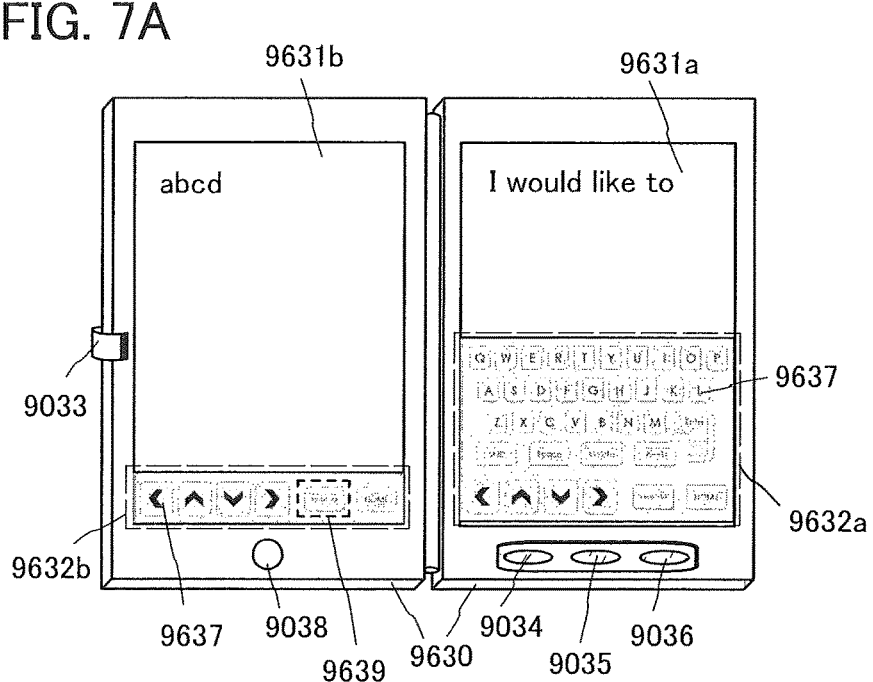
FIGS. 7A to 7C illustrate an electronic device.
Figure 7B:
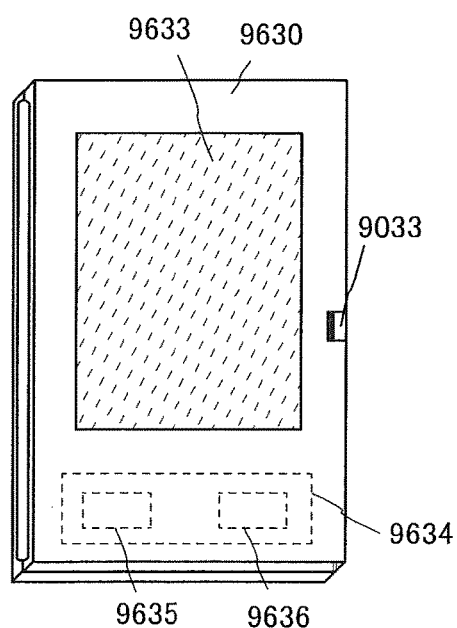

FIGS. 7A and 7B illustrate a tablet terminal that can be folded. In FIG. 7A, the tablet terminal is opened, and includes a housing 9630, a display portion 9631a, a display portion 9631b, a switch 9034 for switching display modes, a power button 9035, a switch 9036 for switching to power-saving mode, a clip 9033, and an operation button 9038. The tablet terminal is manufactured using the light-emitting device for either the display portion 9631a or the display portion 9631b or both.

Figure 10:
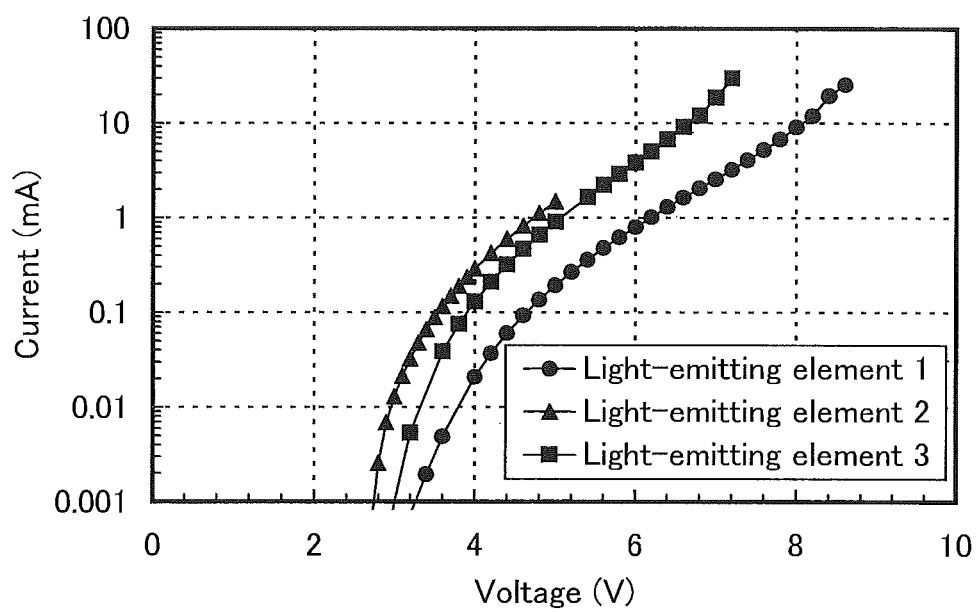
FIG. 10 is a graph showing voltage-current characteristics of the light-emitting element 1, the light-emitting element 2, and the light-emitting element 3.

Part of the display portion 9631a can be a touch panel area 9632a and data can be input when a displayed operation key 9637 is touched. Note that FIG. 10 shows, as an example, that half of the area of the display portion 9631a has only a display function and the other half of the area has a touch panel function. However, the structure of the display portion 9631a is not limited to this, and all the area of the display portion 9631a may have a touch panel function. For example, all the area of the display portion 9631a can display keyboard buttons and serve as a touch panel while the display portion 9631b can be used as a display screen.

Like the display portion 9631a, part of the display portion 9631b can be a touch panel area 9632b. When a finger, a stylus, or the like touches the place where a button 9639 for switching to keyboard display is displayed in the touch panel, keyboard buttons can be displayed on the display portion 9631b.

Touch input can be performed concurrently on the touch panel areas 9632a and 9632b.

The switch 9034 for switching display modes can switch display orientation (e.g., between landscape mode and portrait mode) and select a display mode (switch between monochrome display and color display), for example. With the switch 9036 for switching to power-saving mode, the luminance of display can be optimized in accordance with the amount of external light at the time when the tablet terminal is in use, which is detected with an optical sensor incorporated in the tablet terminal. The tablet terminal may include another detection device such as a sensor for detecting orientation (e.g., a gyroscope or an acceleration sensor) in addition to the optical sensor.

Although the display portion 9631a and the display portion 9631b have the same display area in FIG. 7A, one embodiment of the present invention is not limited to this example. The display portion 9631a and the display portion 9631b may have different areas or different display quality. For example, one of them may be a display panel that can display higher-definition images than the other.

FIG. 7B illustrates the tablet terminal folded, which includes the housing 9630, a solar battery 9633, a charge and discharge control circuit 9634, a battery 9635, and a DCDC converter 9636. Note that FIG. 7B shows an example in which the charge and discharge control circuit 9634 includes the battery 9635 and the DCDC converter 9636.

Since the tablet terminal can be folded in two, the housing 9630 can be closed when the tablet terminal is not in use. Thus, the display portions 9631a and 9631b can be protected, thereby providing a tablet terminal with high endurance and high reliability for long-term use.

The tablet terminal illustrated in FIGS. 7A and 7B can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs).

The solar battery 9633, which is attached on the surface of the tablet terminal, supplies electric power to a touch panel, a display portion, an image signal processor, and the like. Note that a structure in which the solar battery 9633 is provided on one or both surfaces of the housing 9630 is preferable because the battery 9635 can be charged efficiently. When a lithium ion battery is used as the battery 9635, there is an advantage of downsizing or the like.

Figure 7C:
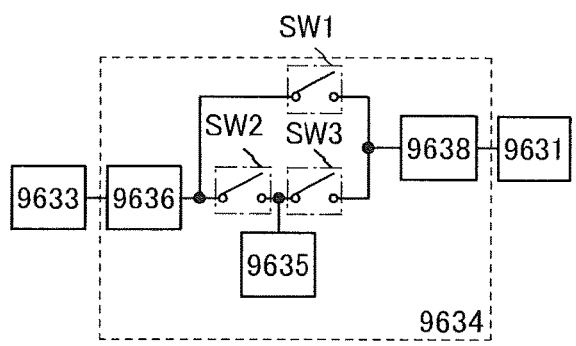

The structure and operation of the charge and discharge control circuit 9634 illustrated in FIG. 7B are described with reference to a block diagram of FIG. 7C. FIG. 7C illustrates the solar battery 9633, the battery 9635, the DCDC converter 9636, a converter 9638, switches SW1 to SW3, and the display portion 9631. The battery 9635, the DCDC converter 9636, the converter 9638, and the switches SW1 to SW3 correspond to the charge and discharge control circuit 9634 in FIG. 7B.

First, an example of operation in the case where power is generated by the solar battery 9633 using external light is described. The voltage of power generated by the solar battery is raised or lowered by the DCDC converter 9636 so that the power has a voltage for charging the battery 9635. When the display portion 9631 is operated with the power from the solar battery 9633, the switch SW1 is turned on and the voltage of the power is raised or lowered by the converter 9638 to a voltage needed for operating the display portion 9631. In addition, when display on the display portion 9631 is not performed, the switch SW1 may be turned off and the switch SW2 may be turned on so that the battery 9635 is charged.

Here, the solar battery 9633 is shown as an example of a power generation means; however, there is no particular limitation on a way of charging the battery 9635, and the battery 9635 may be charged with another power generation means such as a piezoelectric element or a thermoelectric conversion element (Peltier element). For example, the battery 9635 may be charged with a non-contact power transmission module that transmits and receives power wirelessly (without contact) to charge the battery or with a combination of other charging means.

It is needless to say that one embodiment of the present invention is not limited to the electronic device illustrated in FIGS. 7A to 7C as long as the display portion described in the above embodiment is included.

As described above, the electronic devices can be obtained by application of the light-emitting device according to one embodiment of the present invention. The light-emitting device has a remarkably wide application range, and can be applied to electronic devices in a variety of fields.

Note that the structure described in this embodiment can be combined as appropriate with any of the structures described in the other embodiments.

Embodiment 6

In this embodiment, examples of a lighting device to which a light-emitting device including a light-emitting element of one embodiment of the present invention is applied, are described with reference to FIG. 8.

Figure 8:
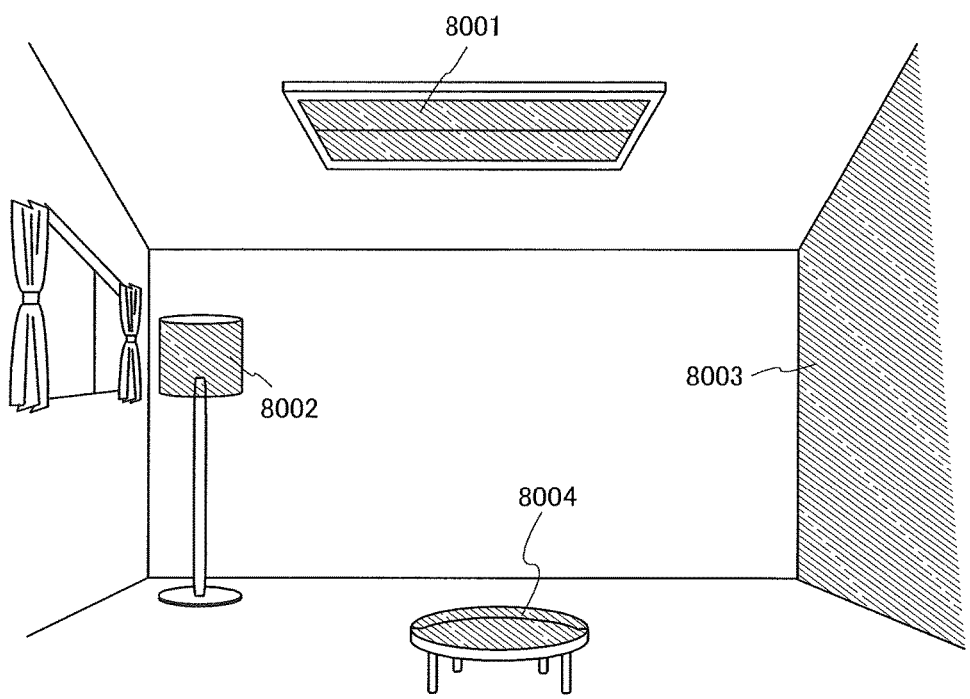
FIG. 8 illustrates lighting devices.

FIG. 8 illustrates an example in which the light-emitting device is used as an indoor lighting device 8001. Note that since the area of the light-emitting device can be increased, a lighting device having a large area can also be formed. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Further, a wall of the room may be provided with a large-sized lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

In this manner, a variety of lighting devices to which the light-emitting device is applied can be obtained. Note that such lighting devices are also embodiments of the present invention.

Note that the structure described in this embodiment can be combined as appropriate with any of the structures described in the other embodiments.

Example 1

Figure 9:
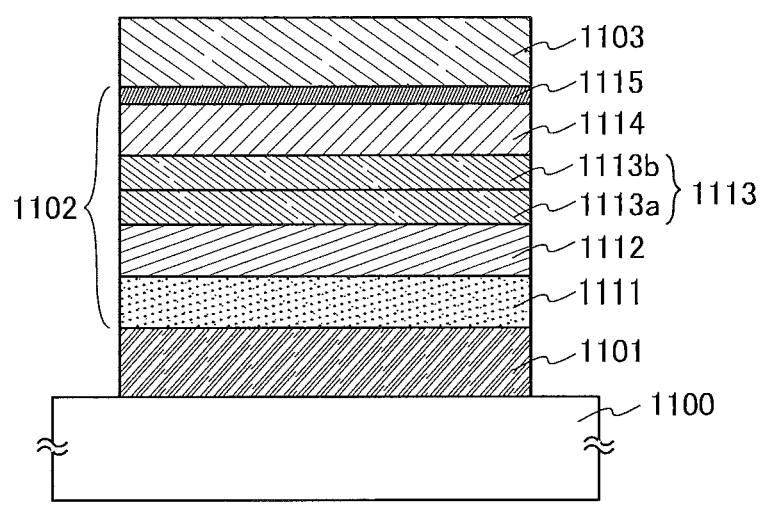
FIG. 9 illustrates a structure of a light-emitting element.

In this example, light-emitting elements which are each one embodiment of the present invention are fabricated, and the measurement results of the characteristics thereof are shown. Note that a light-emitting element 1 in this example is a comparative light-emitting element for comparison with a light-emitting element 2 and a light-emitting element 3. In this example, in light-emitting layers of the light-emitting elements, the HOMO level of a host material (10,15-dihydro-5,10,15-triphenyl-5H-diindolo[3,2-a:3',2'-c]carbazole (abbreviation: P3Dic)) which is used for each of the light-emitting element 2 and the light-emitting element 3 is higher than the HOMO level of a host material (9-phenyl-9H-3-(9-phenyl-9H-carbazol-3-yl)carbazole (abbreviation:

PCCP)) used for the light-emitting element 1. That is, in the light-emitting element 2 and the light-emitting element 3, the difference between the HOMO level of the host material (P3Dic (abbreviation)) and the HOMO level of the guest material ([Ir(mpptz-dmp)$_3$] (abbreviation)) is lower than or equal to 0.3 eV; in the light-emitting element 1 which is a comparative light-emitting element, the difference is higher than 0.3 eV. The light-emitting elements fabricated in this example are described with reference to FIG. 9. Chemical formulae of materials used in this example are shown below.

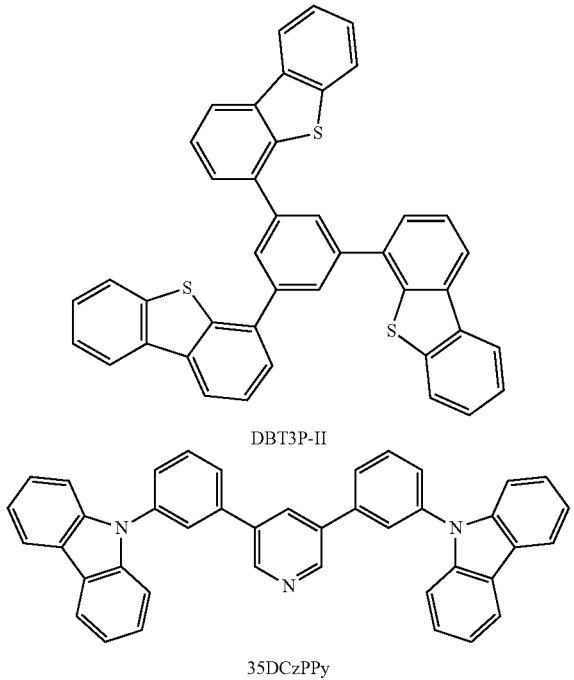

DBT3P-II

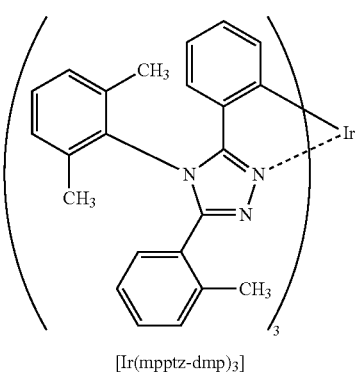

35DCzPPy

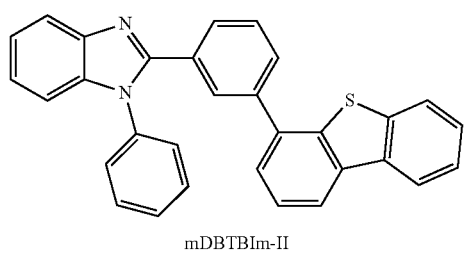

[Ir(mpptz-dmp)$_3$]

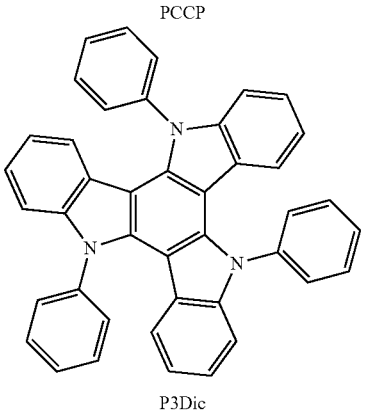

mDBTBIm-II

-continued

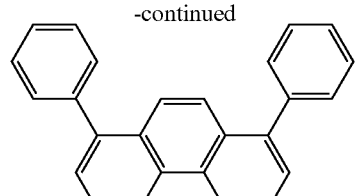

Bphen

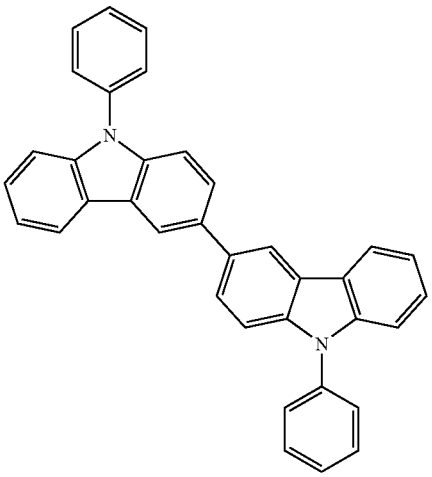

PCCP

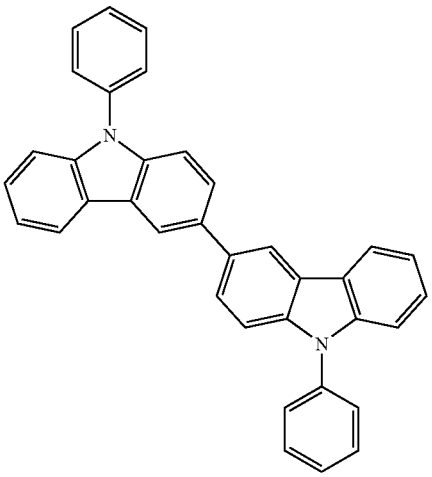

P3Dic

[Fabrication of Light-Emitting Element 1, Light-Emitting Element 2, and Light-Emitting Element 3]

First, a film of indium oxide-tin oxide containing silicon oxide (ITSO) was formed over a glass substrate 1100 by a sputtering method, so that a first electrode 1101 functioning as an anode was formed. The thickness was 110 nm and the electrode area was 2 mm×2 mm.

Next, as pretreatment for forming the light-emitting element over the substrate 1100, the surface of the substrate was washed, baked at 200° C. for one hour, and subjected to UV ozone treatment for 370 seconds.

After that, the substrate 1100 was transferred into a vacuum evaporation apparatus where the pressure had been reduced to approximately 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which a hole-injection layer 1111, a hole-transport layer 1112, a light-emitting layer 1113, an electron-transport layer 1114, and an electron-injection layer 1115 which are included in an EL layer 1102 are sequentially formed by a vacuum evaporation method.

After reducing the pressure of the vacuum evaporation apparatus to $10^{-4}$ Pa, 1,3,5-tri(dibenzothiophen-4-yl)benzene (abbreviation: DBT3P-II) and molybdenum oxide(VI) were co-evaporated with a mass ratio of DBT3P-II (abbreviation) to molybdenum oxide being 4:2, whereby the hole-injection layer 1111 was formed over the first electrode 1101. The thickness was set to 60 nm. Note that a co-evaporation method is an evaporation method in which a plurality of different substances is concurrently vaporized from respective different evaporation sources.

Then, in the case of the light-emitting element 1, 9-phenyl-9H-3-(9-phenyl-9H-carbazol-3-yl)carbazole (abbreviation: PCCP) was deposited by evaporation to a thickness of 20 nm, whereby the hole-transport layer 1112 was formed. In the case of the light-emitting element 2 and the light-emitting element 3, 10,15-dihydro-5,10,15-triphenyl-5H-diindolo[3,2-a:3',2'-c]carbazole (abbreviation: P3Dic) was deposited by evaporation to a thickness of 20 nm, whereby the hole-transport layer 1112 was formed.

Next, the light-emitting layer 1113 was formed over the hole-transport layer 1112.

For the light-emitting element 1, PCCP (abbreviation), 3,5-bis[3-(9H-carbazol-9-yl)phenyl]pyridine (abbreviation: 35DCzPPy), and tris{2-[5-(2-methylphenyl)-4-(2,6-dimethylphenyl)-4H-1,2,4-triazol-3-yl-κN2]phenyl-κC}iridium (III) (abbreviation: [Ir(mpptz-dmp)$_3$]) were co-evaporated to a thickness of 30 nm with a mass ratio of PCCP (abbreviation) to 35DCzPPy (abbreviation) and [Ir(mpptz-dmp)$_3$] (abbreviation) being 1:0.3:0.06 to form a first light-emitting layer 1113a, and then further co-evaporated to a thickness of 10 nm with a mass ratio of 35DCzPPy (abbreviation) to [Ir(mpptz-dmp)$_3$] (abbreviation) being 1:0.06 to form a second light-emitting layer 1113b; thus, the light-emitting layer 1113 which is a stacked structure of the first light-emitting layer 1113a and the second light-emitting layer 1113b was formed.

For the light-emitting element 2, P3Dic (abbreviation), 35DCzPPy (abbreviation), and [Ir(mpptz-dmp)$_3$] (abbreviation) were co-evaporated to a thickness of 30 nm with a mass ratio of P3Dic (abbreviation) to 35DCzPPy (abbreviation) and [Ir(mpptz-dmp)$_3$] (abbreviation) being 1:0.3:0.06 to form a first light-emitting layer 1113a, and then further co-evaporated to a thickness of 10 nm with a mass ratio of 35DCzPPy (abbreviation) to Ir(mpptz-dmp)$_3$ (abbreviation) being 1:0.06 to form a second light-emitting layer 1113b; thus, the light-emitting layer 1113 which is a stacked structure of the first light-emitting layer 1113a and the second light-emitting layer 1113b was formed.

For the light-emitting element 3, P3Dic (abbreviation), 35DCzPPy (abbreviation), and [Ir(mpptz-dmp)$_3$] (abbreviation) were co-evaporated to a thickness of 30 nm with a mass ratio of P3Dic (abbreviation) to 35DCzPPy (abbreviation) and [Ir(mpptz-dmp)$_3$] (abbreviation) being 0.3:1:0.06 to form a first light-emitting layer 1113a, and then further co-evaporated to a thickness of 10 nm with a mass ratio of 35DCzPPy (abbreviation) to Ir(mpptz-dmp)$_3$ (abbreviation) being 1:0.06 to form a second light-emitting layer 1113b; thus, the light-emitting layer 1113 which is a stacked structure of the first light-emitting layer 1113a and the second light-emitting layer 1113b was formed.

Next, after evaporating 2-[3-(dibenzothiophen-4-yl)phenyl]-1-phenyl-1H-benzimidazole (abbreviation: mDBTBIm-II) to a thickness of 10 nm over the light-emitting layer 1113, bathophenanthroline (abbreviation: BPhen) was further evaporated to a thickness of 15 nm, whereby the electron-transport layer 1114 having a stacked structure was formed. Furthermore, lithium fluoride was evaporated to a thickness of 1 nm over the electron-transport layer 1114, whereby the electron-injection layer 1115 was formed.

Finally, aluminum was deposited by evaporation to a thickness of 200 nm over the electron-injection layer 1115 to form the second electrode 1103 serving as a cathode; thus, the light-emitting element 1, the light-emitting element 2, and the light-emitting element 3 were obtained. Note that, in the above evaporation process, evaporation was all performed by a resistance heating method.

Table 1 shows element structures of the light-emitting element 1, the light-emitting element 2, and the light-emitting element 3.

TABLE 1

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 1 | ITSO (110 nm) | DBT3P-II:MoOx (4:2 60 nm) | PCCP (20 nm) | * | mDBTBIm-II (10 nm) | Bphen (15 nm) | LiF (1 nm) | Al (200 nm) |
| Light-emitting element 2 | | | P3Dic (20 nm) | ** | | | | |
| Light-emitting element 3 | | | | *** | | | | |

\* PCCP:35DCzPPy:[Ir(mpptz-dmp)$_3$] (1:0.3:0.06 30 nm)
\*\* P3Dic:35DCzPPy:[Ir(mpptz-dmp)$_3$] (1:0.3:0.06 30 nm)
\*\*\* P3Dic:35DCzPPy:[Ir(mpptz-dmp)$_3$] (0.3:1:0.06 30 nm)
\*\*\*\* 35DCzPPy:[Ir(mpptz-dmp)$_3$] (1:0.06 10 nm)

Further, the light-emitting element 1 fabricated, the light-emitting element 2 fabricated, and the light-emitting element 3 fabricated were sealed in a glove box containing a nitrogen atmosphere so as not to be exposed to the air (specifically, a sealant was applied onto outer edges of the elements and heat treatment was performed at 80° C. for 1 hour at the time of sealing).

[Operation Characteristics of Light-Emitting Element 1, Light-Emitting Element 2, and Light-Emitting Element 3]

Operation characteristics of the light-emitting element 1 fabricated, the light-emitting element 2 fabricated, and the light-emitting element 3 fabricated were measured. Note that the measurement was carried out at room temperature (in an atmosphere kept at 25° C.).

Figure 11:
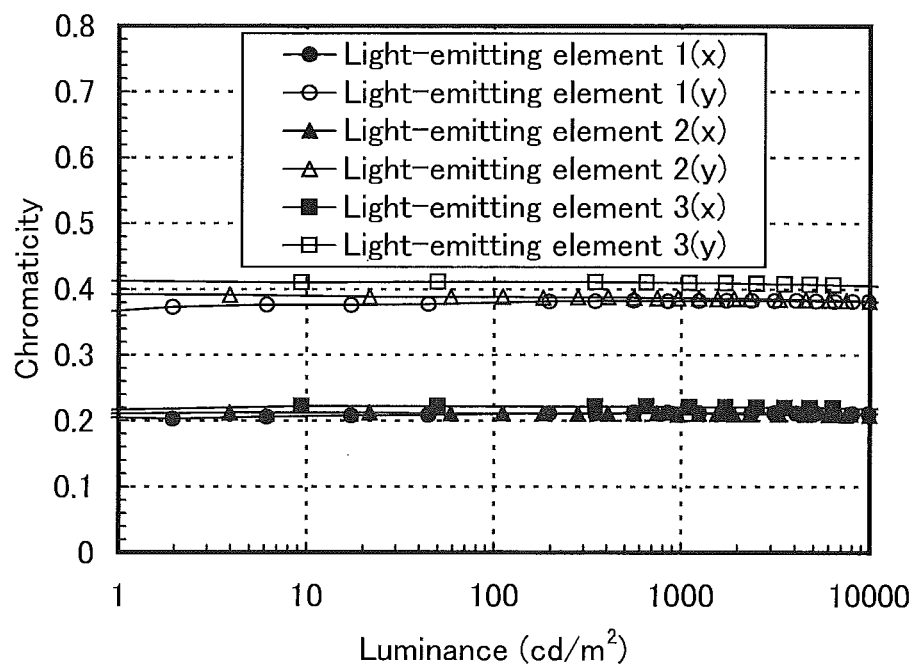
FIG. 11 is a graph showing luminance-chromaticity characteristics of the light-emitting element 1, the light-emitting element 2, and the light-emitting element 3.
Figure 12:
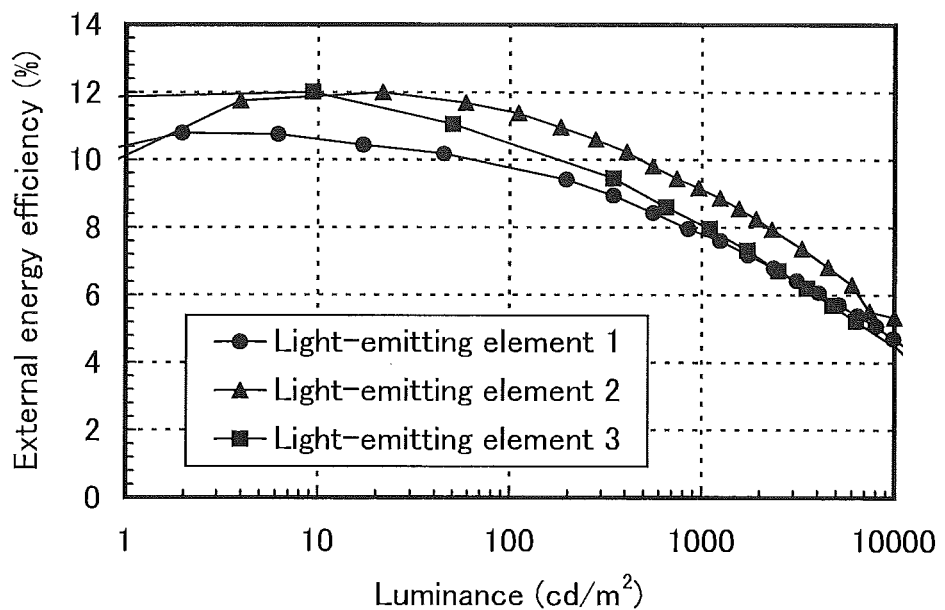
FIG. 12 is a graph showing luminance-external energy efficiency characteristics of the light-emitting element 1, the light-emitting element 2, and the light-emitting element 3.

FIG. 10 shows voltage-current characteristics of the light-emitting element 1, the light-emitting element 2, and the light-emitting element 3. In FIG. 10, the vertical axis represents current (mA) and the horizontal axis represents voltage (V). Further, FIG. 11 shows luminance-chromaticity characteristics of the light-emitting element 1, the light-emitting element 2, and the light-emitting element 3. In FIG. 11, the vertical axis represents chromaticity coordinate and the horizontal axis represents luminance ($cd/m^2$). FIG. 12 shows luminance-external energy efficiency characteristics of the light-emitting element 1, the light-emitting element 2, and the light-emitting element 3. In FIG. 12, the vertical axis represents external energy efficiency (%) and the horizontal axis represents luminance ($cd/m^2$).

According to FIG. 10, it is found that the light-emitting element 2 and the light-emitting element 3 which are each one embodiment of the present invention have lower driving voltage than the light-emitting element 1 which is a comparative light-emitting element. In addition, according to FIG. 12, it is found that the light-emitting element 2 and the light-emitting element 3 have higher external energy efficiency than the light-emitting element 1. This is considered to be because P3Dic (abbreviation) used for the light-emitting layer of each of the light-emitting element 2 and the light-emitting element 3 has a higher HOMO level than PCCP used for the light-emitting layer of the light-emitting element 1 (has a HOMO level close to [Ir(mpptz-dmp)$_3$] (abbreviation)) and also has a high T1 level, whereby the light-emitting element 2 and the light-emitting element 3 have low driving voltage and the luminous efficiency is improved. The above reason is supported by that the light-emitting element 2 containing more P3Dic (abbreviation) in the light-emitting layer than the light-emitting element 3 has lower driving voltage and higher efficiency than the light-emitting element 3.

In addition, according to FIG. 11, it is found that the chromaticity of each of the light-emitting element 2 and the light-emitting element 3 is substantially the same as that of the light-emitting element 1. Therefore, it is found that characteristics of the light-emitting element 2 and the light-emitting element 3 which are one embodiment of the present invention can be improved as compared to those of the light-emitting element 1 while the chromaticity that is substantially the same as that of the light-emitting element 1 is maintained. Further, the above results indicate that the light-emitting element 2 and the light-emitting element 3 have almost no color change at each luminance and therefore have a favorable carrier balance.

Table 2 shows initial values of main characteristics of the light-emitting element 1, the light-emitting element 2, and the light-emitting element 3 at a luminance of about 1000 $cd/m^2$.

Figure 13:
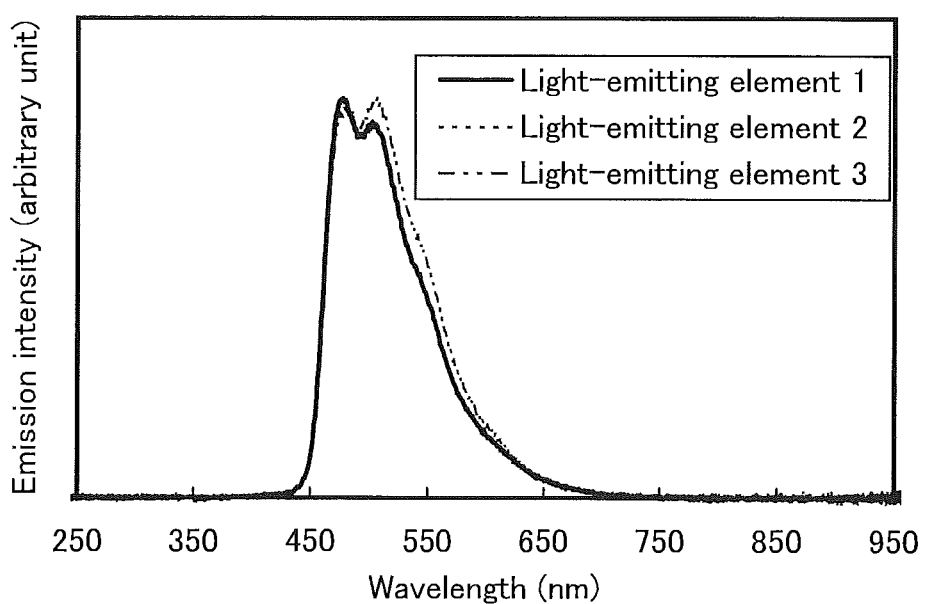
FIG. 13 shows emission spectra of the light-emitting element 1, the light-emitting element 2, and the light-emitting element 3.

FIG. 13 shows emission spectra of the light-emitting element 1, the light-emitting element 2, and the light-emitting element 3 which were obtained by application of a current of 0.1 mA. As shown in FIG. 13, it is found that each of the light-emitting element 1, the light-emitting element 2, and the light-emitting element 3 has peaks of emission spectrum at around 481 nm and at around 508 nm; these peaks derive from the emission of [Ir(mpptz-dmp)$_3$] (abbreviation) in the light-emitting layer 1113.

It was thus found that P3Dic (abbreviation) has a sufficiently high T1 level to use as a blue host material. That is, P3Dic (abbreviation) can be used as a host material in a light-emitting layer of a phosphorescent light-emitting element having an emission peak in a visible region.

Example 2

In this example, light-emitting elements which are each one embodiment of the present invention are fabricated, and the measurement results of the characteristics thereof are shown. Note that a light-emitting element 4 in this example is a comparative light-emitting element for comparison with a light-emitting element 5. Note that FIG. 9, which is used for the description of the light-emitting element 1, the light-emitting element 2, and the light-emitting element 3 in Example 1, is used for describing the light-emitting element 4 and the light-emitting element 5 in this example. Chemical formulae of materials used in this example are shown below.

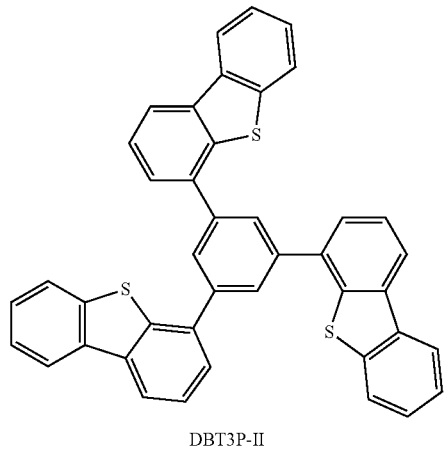

DBT3P-II

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) | External energy efficiency (%) |
|---|---|---|---|---|---|---|---|---|---|
| Light-emitting element 1 | 4.6 | 0.093 | 2.3 | (0.21, 0.38) | 850 | 37 | 25 | 15 | 8.0 |
| Light-emitting element 2 | 3.6 | 0.12 | 2.9 | (0.21, 0.39) | 960 | 33 | 29 | 14 | 9.2 |
| Light-emitting element 3 | 4 | 0.13 | 3.3 | (0.22, 0.41) | 1100 | 34 | 27 | 13 | 8.0 |

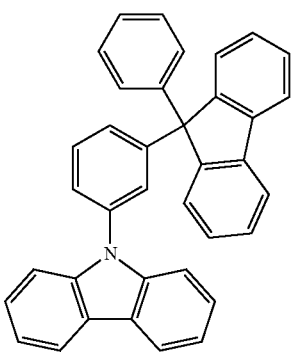

mCzFLP

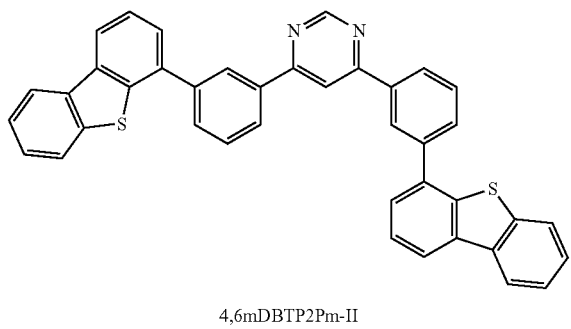

4,6mDBTP2Pm-II

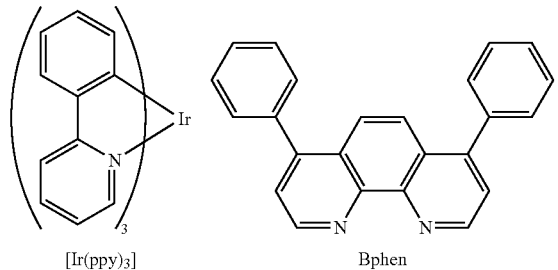

[Ir(ppy)₃]  Bphen

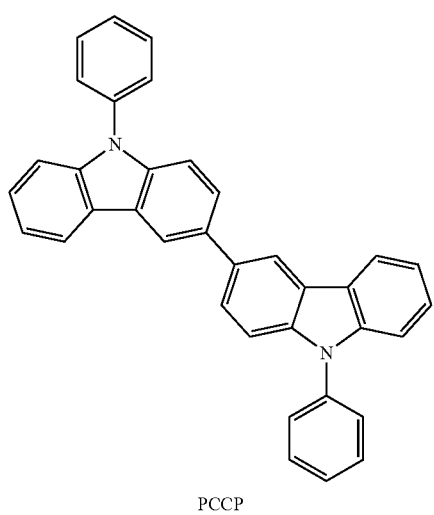

PCCP

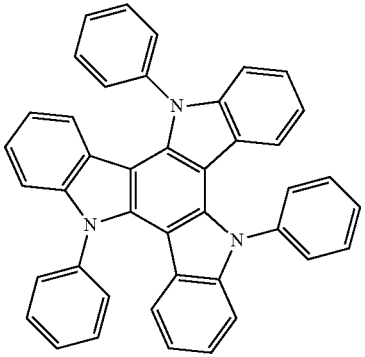

P3Dic

[Fabrication of Light-Emitting Element 4 and Light-Emitting Element 5]

First, indium tin oxide containing silicon oxide (ITSO) was deposited over a glass substrate 1100 by a sputtering method, so that a first electrode 1101 functioning as an anode was formed. The thickness was 110 nm and the electrode area was 2 mm×2 mm.

Next, as pretreatment for forming the light-emitting element over the substrate 1100, the surface of the substrate was washed, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which a hole-injection layer 1111, a hole-transport layer 1112, a light-emitting layer 1113, an electron-transport layer 1114, and an electron-injection layer 1115 which are included in an EL layer 1102 are sequentially formed by a vacuum evaporation method.

After reducing the pressure of the vacuum evaporation apparatus to $10^{-4}$ Pa, 1,3,5-tri(dibenzothiophen-4-yl)benzene (abbreviation: DBT3P-II) and molybdenum oxide(VI) were co-evaporated with a mass ratio of DBT3P-II (abbreviation) to molybdenum oxide being 4:2, whereby the hole-injection layer 1111 was formed over the first electrode 1101. The thickness was 60 nm Note that a co-evaporation method is an evaporation method in which a plurality of different substances is concurrently vaporized from respective different evaporation sources.

Next, 9-[3-(9-phenyl-9H-fluoren-9-yl)phenyl]-9H-carbazole (abbreviation: mCzFLP) was evaporated to a thickness of 20 nm, so that the hole-transport layer 1112 was formed.

Next, the light-emitting layer 1113 was formed over the hole-transport layer 1112.

For the light-emitting element 4, 4,6-bis[3-(dibenzothiophen-4-yl)phenyl]pyrimidine (abbreviation: 4,6mDBTP2Pm-II), PCCP (abbreviation), and tris(2-phenylpyridinato)iridium(III) (abbreviation: [Ir(ppy)₃]) were co-evaporated to a thickness of 20 nm with a mass ratio of 4,6mDBTP2Pm-II (abbreviation) to PCCP (abbreviation) and [Ir(ppy)$_3$] (abbreviation) being 0.7:0.3:0.06 to form a first light-emitting layer 1113a, and then further co-evaporated to a thickness of 20 nm with a mass ratio of 4,6mDBTP2Pm-II (abbreviation) to PCCP (abbreviation) and [Ir(ppy)$_3$] (abbreviation) being 0.8:0.2:0.06 to form a second light-emitting layer 1113b; thus, the light-emitting layer 1113 which is a stacked structure of the first light-emitting layer 1113a and the second light-emitting layer 1113b was formed.

For the light-emitting element 5, 4,6-bis[3-(dibenzothiophen-4-yl)phenyl]pyrimidine (abbreviation: 4,6mDBTP2Pm-II), 10,15-dihydro-5,10,15-triphenyl-5H-diindolo[3,2-a:3',2'-c] carbazole (abbreviation: P3Dic), and tris(2-phenylpyridinato)iridium(III) (abbreviation: [Ir(ppy)$_3$]) were co-evaporated to a thickness of 20 nm with a mass ratio of 4,6mDBTP2Pm-II (abbreviation) to P3Dic (abbreviation) and [Ir(ppy)$_3$] (abbreviation) being 0.7:0.3:0.06 to form a first light-emitting layer 1113a, and then further co-evaporated to a thickness of 20 nm with a mass ratio of 4,6mDBTP2Pm-II (abbreviation) to P3Dic (abbreviation) and [Ir(ppy)$_3$] (abbreviation) being 0.8:0.2:0.06 to form a second light-emitting layer 1113b; thus, the light-emitting layer 1113 which is a stacked structure of the first light-emitting layer 1113a and the second light-emitting layer 1113b was formed.

Then, 4,6mDBTP2Pm-II (abbreviation) was evaporated to a thickness of 10 nm over the light-emitting layer 1113 and bathophenanthroline (abbreviation: Bphen) was evaporated to a thickness of 20 nm, whereby the electron-transport layer 1114 having a stacked structure was formed. Furthermore, lithium fluoride was evaporated to a thickness of 1 nm over the electron-transport layer 1114, whereby the electron-injection layer 1115 was formed.

Finally, aluminum was evaporated to a thickness of 200 nm over the electron-injection layer 1115 to form a second electrode 1103 serving as a cathode; thus, the light-emitting element 4 and the light-emitting element 5 were obtained. Note that, in the above evaporation process, evaporation was all performed by a resistance heating method.

Table 3 shows element structures of the light-emitting element 4 and the light-emitting element 5.

Further, the light-emitting element 4 fabricated and the light-emitting element 5 fabricated were sealed in a glove box containing a nitrogen atmosphere so as not to be exposed to the air (specifically, a sealant was applied onto outer edges of the elements and heat treatment was performed at 80° C. for 1 hour at the time of sealing).

[Operation Characteristics of Light-Emitting Element 4 and Light-Emitting Element 5]

Operation characteristics of the light-emitting element 4 fabricated and the light-emitting element 5 fabricated were measured. Note that the measurement was carried out at room temperature (in an atmosphere kept at 25° C.).

Figure 14:
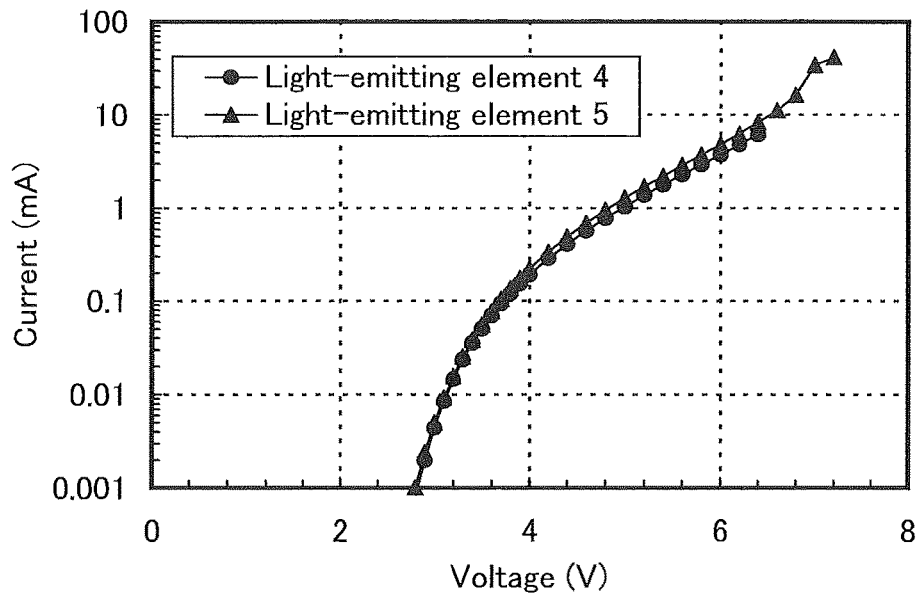
FIG. 14 is a graph showing voltage-current characteristics of the light-emitting element 4 and the light-emitting element 5.
Figure 15:
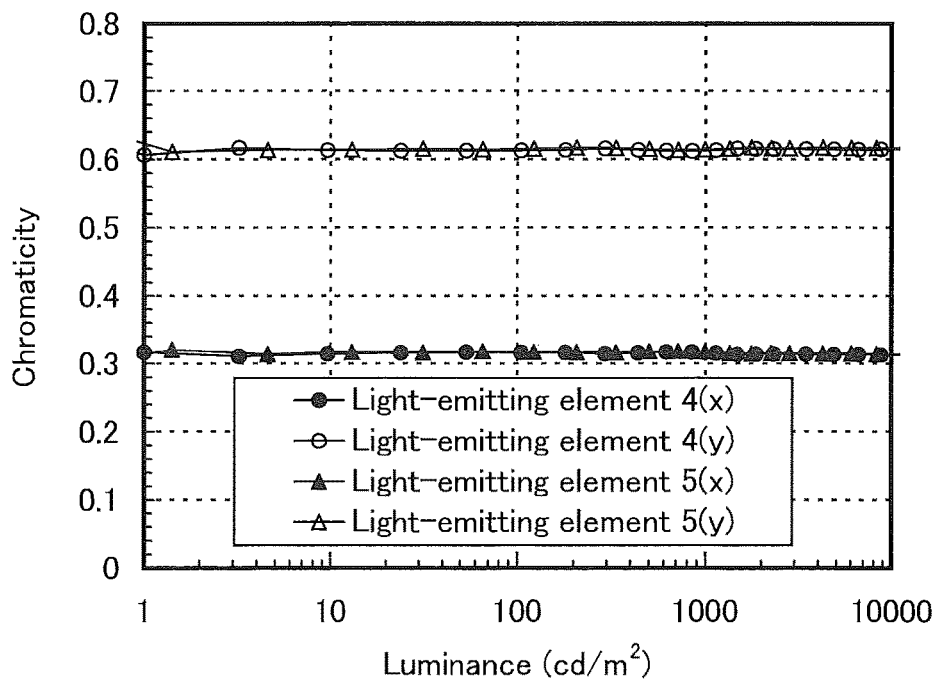
FIG. 15 is a graph showing luminance-chromaticity characteristics of the light-emitting element 4 and the light-emitting element 5.
Figure 16:
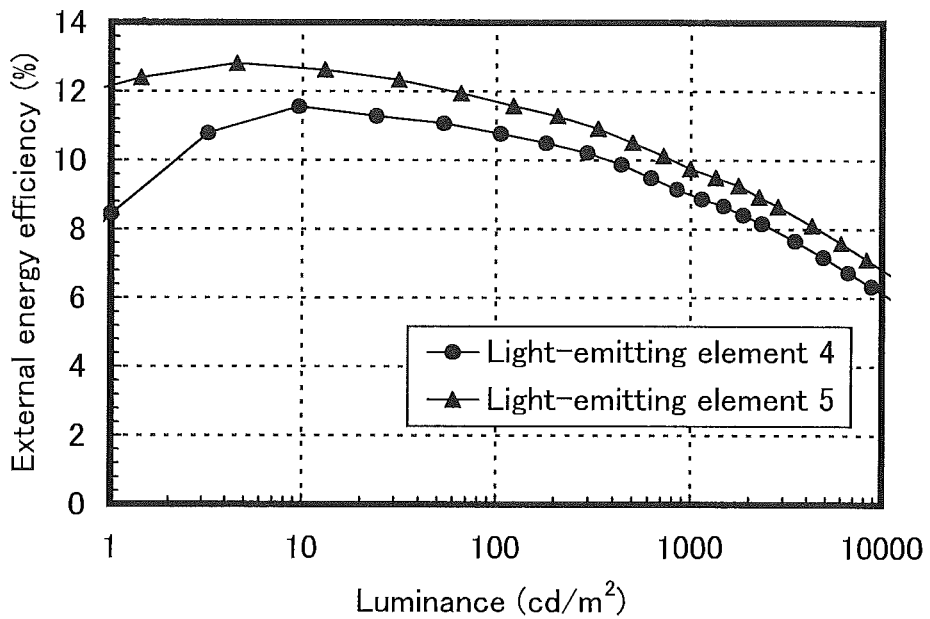
FIG. 16 is a graph showing luminance-external energy efficiency characteristics of the light-emitting element 4 and the light-emitting element 5.

FIG. 14 shows voltage-current characteristics of the light-emitting element 4 and the light-emitting element 5. In FIG. 14, the vertical axis represents current (mA) and the horizontal axis represents voltage (V). Further, FIG. 15 shows luminance-chromaticity characteristics of the light-emitting element 4 and the light-emitting element 5. In FIG. 15, the vertical axis represents chromaticity coordinate and the horizontal axis represents luminance (cd/m$^2$). FIG. 16 shows luminance-external energy efficiency characteristics of the light-emitting element 4 and the light-emitting element 5. In FIG. 16, the vertical axis represents external energy efficiency (%) and the horizontal axis represents luminance (cd/m$^2$).

According to FIG. 16, it is found that the light-emitting element 5 has higher external energy efficiency than the light-emitting element 4. This is considered to be because P3Dic used for the light-emitting layer of the light-emitting element 5 has a higher HOMO level and a higher carrier-transport property than PCCP used for the light-emitting layer of the light-emitting element 4; therefore, a recombination region is enlarged and a carrier balance is improved in the light-emitting element 5.

In addition, according to FIG. 15, it is found that the chromaticity of the light-emitting element 5 is substantially the same as that of the light-emitting element 4. Therefore, it is found that characteristics of the light-emitting element 5 which is one embodiment of the present invention can be improved as compared to those of the light-emitting element 4 while the chromaticity that is substantially the same as that of the light-emitting element 4 is maintained.

Table 4 shows initial values of main characteristics of the light-emitting element 4 and the light-emitting element 5 at a luminance of about 1000 cd/m$^2$.

TABLE 3

| | First electrode | Hole-injection layer | Hole-transport layer | Light-emitting layer | Electron-transport layer | Electron-injection layer | Second electrode |
|---|---|---|---|---|---|---|---|
| Light-emitting element 4 | ITSO (110 nm) | DBT3P-II:MoO$x$ (4:2 60 nm) | mCzFLP (20 nm) | * | 4,6mDBTP2Pm-II (10 nm) | Bphen (20 nm) | LiF (1 nm) | Al (200 nm) |
| Light-emitting element 5 | | | | ** | | | |

* 4,6mDBTP2Pm-II:PCCP:[Ir(ppy)$_3$] (0.7:0.3:0.06 20 nm\0.8:0.2:0.06 20 nm)

** 4,6mDBTP2Pm-II:P3Dic:[Ir(ppy)$_3$] (0.7:0.3:0.06 20 nm\0.8:0.2:0.06 20 nm)

TABLE 4

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) | External energy efficiency (%) |
|---|---|---|---|---|---|---|---|---|---|
| Light-emitting element 4 | 3.6 | 0.07 | 1.7 | (0.32, 0.61) | 850 | 49 | 43 | 14 | 9.2 |
| Light-emitting element 5 | 3.6 | 0.08 | 1.9 | (0.32, 0.61) | 990 | 51 | 45 | 15 | 9.8 |

Figure 17:
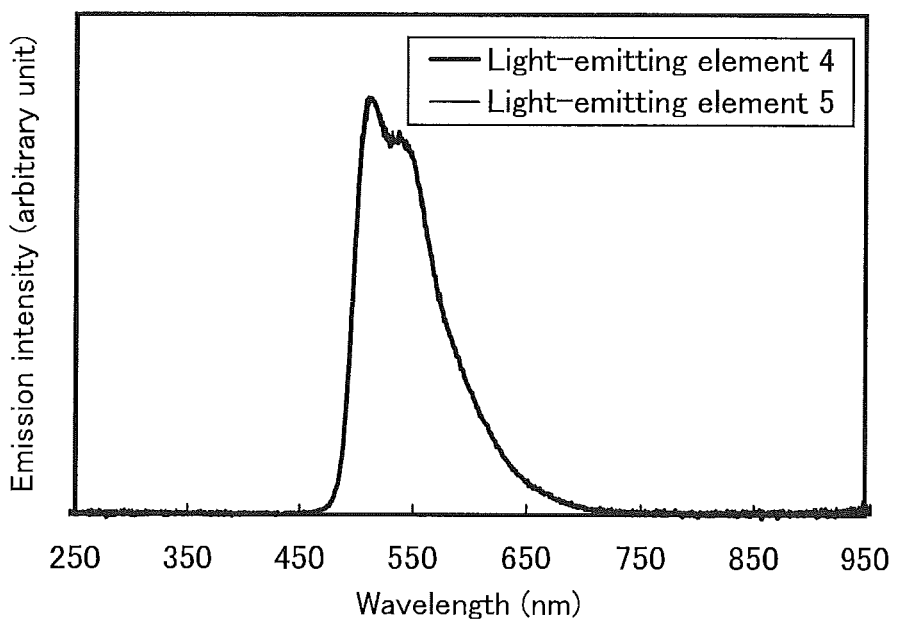
FIG. 17 shows emission spectra of the light-emitting element 4 and the light-emitting element 5.

FIG. 17 shows emission spectra of the light-emitting element 4 and the light-emitting element 5 which were obtained by application of a current of 0.1 mA. As shown in FIG. 17, each of the light-emitting element 4 and the light-emitting element 5 has peaks of emission spectrum at around 517 nm and at around 544 nm; these peak derive from the emission of [Ir(ppy)$_3$] (abbreviation) in the light-emitting layer 1113. Further, the above results indicate that the light-emitting element 4 and the light-emitting element 5 have almost no color change at each luminance and therefore have a favorable carrier balance.

Example 3

In this example, the HOMO levels, the LUMO levels, and the T1 levels of 10,15-dihydro-5,10,15-triphenyl-5H-diindolo[3,2-a:3',2'-c]carbazole (abbreviation: P3Dic (structural formula (100))) which is one embodiment of the present invention; 10,15-dihydro-5,10,15-tribiphenyl-5H-diindolo[3,2-a:3',2'-c] carbazole (abbreviation: BP3Dic (structural formula (104))); compounds represented by the following structural formulae (structural formula (101), structural formula (102), structural formula (103), structural formula (105), structural formula (106), structural formula (107), and structural formula (108)); and 10,15-dihydro-5H-diindolo[3,2-a:3',2'-c]carbazole (abbreviation: Dic (structural formula (R01))) and PCCP (abbreviation) (structural formula (R02)) which are used as comparative examples were calculated by quantum chemistry calculation.

The most stable structures in the singlet state and in the triplet state were obtained by calculation using the density functional theory. As a basis function, 6-311G was applied to all the atoms. Furthermore, to improve calculation accuracy, the p function and the d function as polarization basis sets were added respectively to hydrogen atoms and atoms other than hydrogen atoms. As a functional, B3PW91 was used. Further, each of the HOMO level and the LUMO level of the structure in the singlet state was calculated. Gaussian 09 was used as the quantum chemistry computational program.

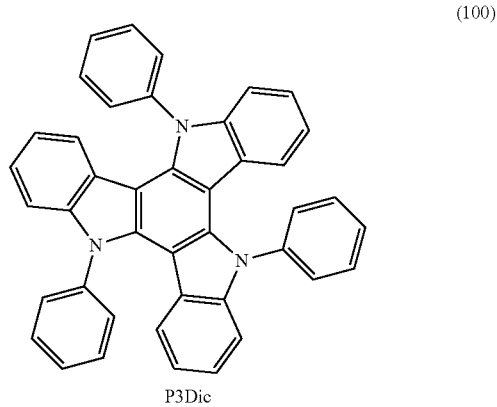

(100)

P3Dic

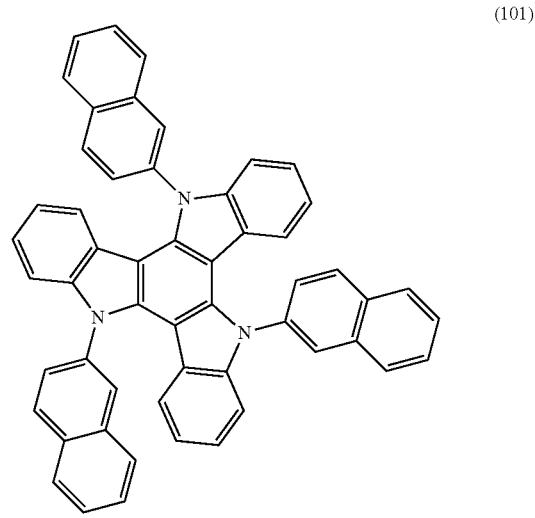

(101)

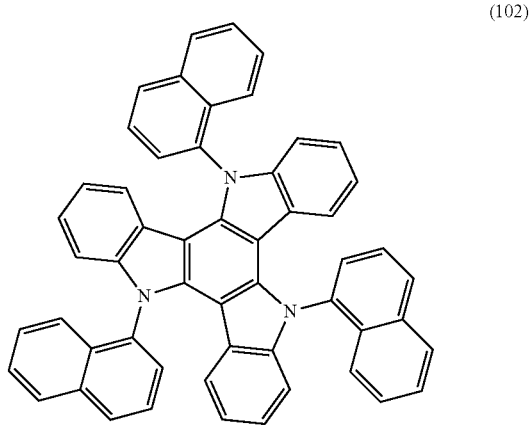

(102)

(103)
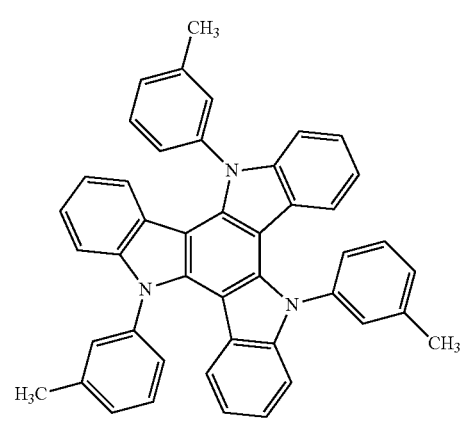
(104)
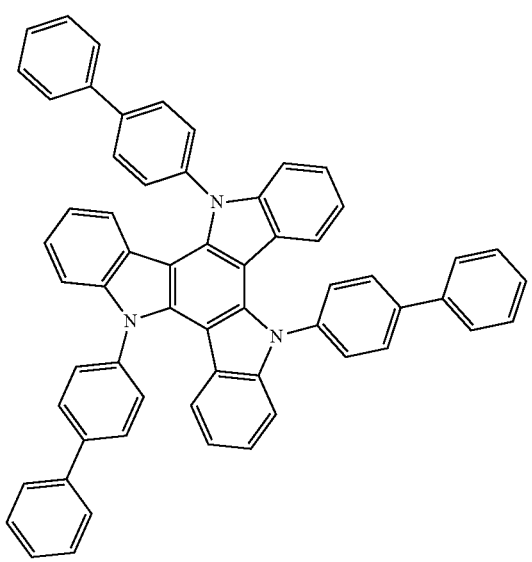
BP3Dic
(105)
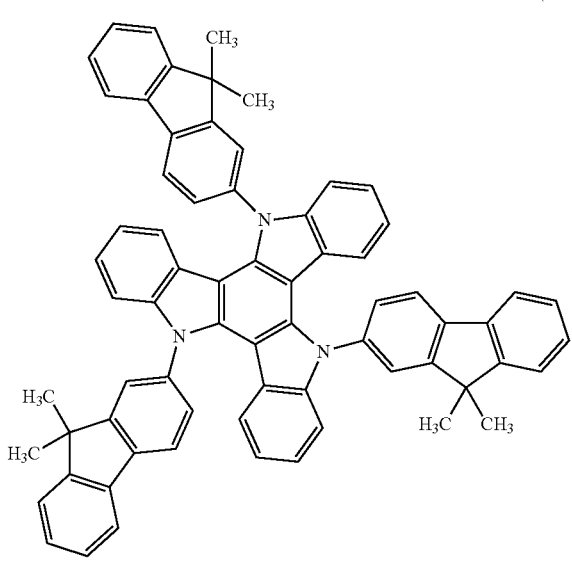
(106)
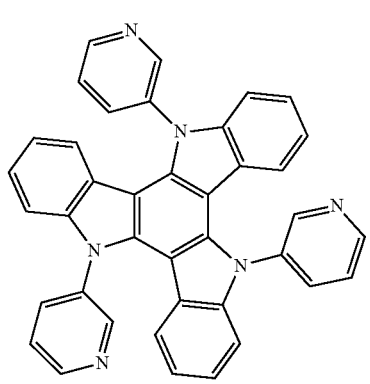
(107)
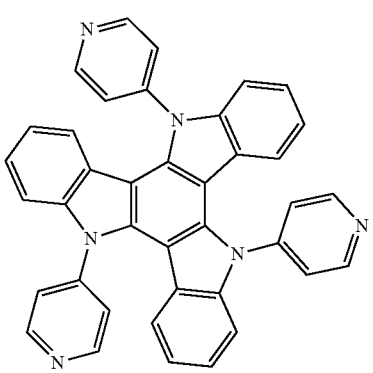
(108)
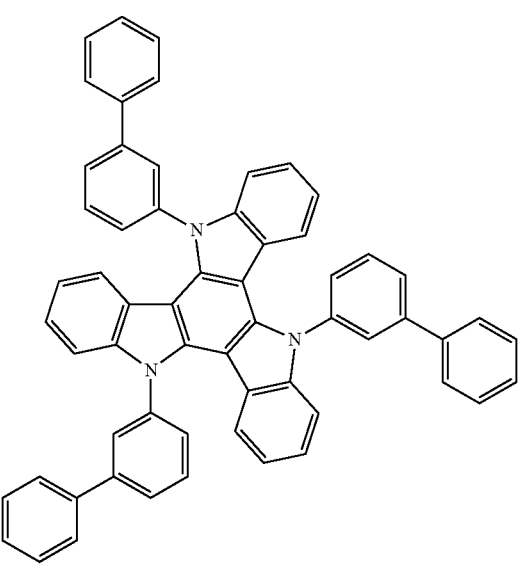
(R01)
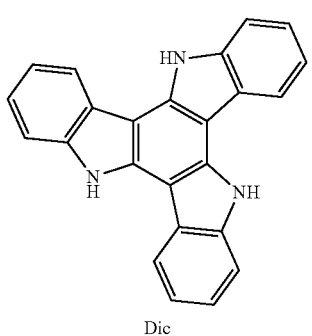
Dic

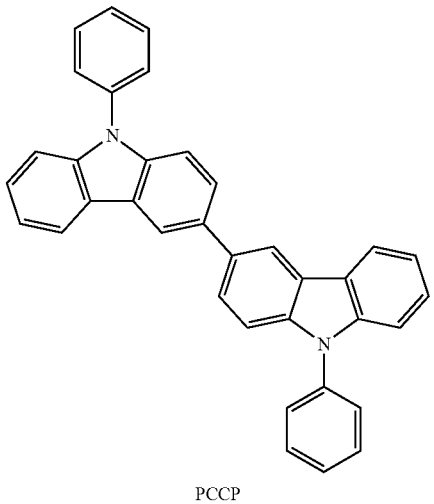

PCCP
(R02)

Table 5 shows the calculation results.

TABLE 5

| Structural formula No. | HOMO level (eV) | LUMO level (eV) | T1 level (eV) |
|---|---|---|---|
| (100) | −5.14 | −0.94 | 2.75 |
| (101) | −5.13 | −1.58 | 2.46 |
| (102) | −5.13 | −1.59 | 2.42 |
| (103) | −5.08 | −0.86 | 2.76 |
| (104) | −5.16 | −1.31 | 2.72 |
| (105) | −5.11 | −1.36 | 2.68 |
| (106) | −5.48 | −1.40 | 2.74 |
| (107) | −5.62 | −1.54 | 2.70 |
| (108) | −5.15 | −1.28 | 2.75 |
| (R01) | −5.29 | −0.86 | 2.90 |
| (R02) | −5.30 | −1.03 | 2.72 |

Table 5 shows that the HOMO level of P3Dic (abbreviation) (structural formula (100)) is high. This is considered to derive from the diindolocarbazole skeleton of Dic (abbreviation) (structural formula (R01)) having a high HOMO level as well as P3Dic (abbreviation). Further, P3Dic (abbreviation) has a structure in which a phenyl group has been bonded to each of the 5-position, the 10-position, and the 15-position of Dic (abbreviation), and the diindolocarbazole skeleton is bonded to the substituents at the 5-position, the 10-position, and the 15-position, whereby extension of conjugation to these substituents can be suppressed; therefore, it is considered that P3Dic (abbreviation) can maintain a high T1 level as well as Dic (abbreviation). Furthermore, it is indicated that, in the case of a structure in which an alkyl group is bonded to the phenyl group of P3Dic (abbreviation) as in a compound shown by the structural formula 103, the HOMO level can be higher than that of P3Dic (abbreviation) while the T1 level is as high as that of P3Dic (abbreviation).

Further, BP3Dic (abbreviation) shown by the structural formula 104 has a structure in which a para-biphenyl group has been bonded to each of the 5-position, the 10-position, and the 15-position of Dic (abbreviation), and has almost the same HOMO level as P3Dic (abbreviation) and has sufficiently high T1 level as well as P3Dic (abbreviation). Furthermore, a compound shown by the structural formula 108 has a structure in which a meta-biphenyl group has been bonded to each of the 5-position, the 10-position, and the 15-position of Dic (abbreviation), and it is found that the compound has almost the same HOMO level as P3Dic (abbreviation) and high T1 level as well as P3Dic (abbreviation).

Further, it is found that the HOMO levels of compounds shown by the structural formula 101, the structural formula 102, and the structural formula 105 are as high as that of P3Dic (abbreviation), and the LUMO level and the T1 level of the P3Dic (abbreviation) are higher than those of the compounds. This is considered to be because in the case of the structure in which a phenyl group has been bonded to each of the 5-position, the 10-position, and the 15-position as in P3Dic (abbreviation), extension of conjugation can be suppressed; however, in the case of a structure in which a substituent that is more likely to allow extension of conjugation than a phenyl group has been bonded to any of the 5-position, the 10-position, and the 15-position as in the compounds shown by the structural formula 101, the structural formula 102, and the structural formula 105, the compound is affected by extension of conjugation; therefore, the LUMO level is low and the T1 level is reduced. It is indicated that the driving voltage of a light-emitting element formed using these compounds can be reduced because the LUMO level is low.

Further, compounds shown by the structural formula 106 and the structural formula 107 each have a structure in which pyrimidine which is a heterocyclic ring is bonded to each of the 5-position, the 10-position, and the 15-position instead of the phenyl group of P3Dic (abbreviation). Note that pyrimidine is considered to have a deeper HOMO level and a deeper LUMO level than P3Dic (abbreviation) because pyrimidine is an electron-deficient skeleton. However, it is found that since pyrimidine is a six-membered ring, conjugation is less likely to extend; therefore, the T1 level of pyrimidine can be as high as that of P3Dic (abbreviation). Accordingly, it is found that the compounds shown by the structural formula 106 and the structural formula 107 are compounds having a bipolar property and a high T1 level. Further, it is found that the compounds are suitably used as a host material for a material emitting phosphorescence having a relatively short wavelength.

Next, table 6 shows values of the HOMO level and the LUMO level obtained by CV measurement, the peak wavelength of fluorescence spectrum, the peak wavelength of phosphorescence spectrum, and the T1 level in a thin film of each of P3Dic (abbreviation) (structural formula (100)), BP3Dic (abbreviation) (structural formula (104)), and PCCP (abbreviation) (structural formula (R02)).

TABLE 6

| Structural formula No. | CV measurement | | fluorescent peak (nm) | phosphorescent peak (nm) | T1 level (eV) |
|---|---|---|---|---|---|
| | HOMO level (eV) | LUMO level (eV) | | | |
| (100) | −5.51 | — | 397 | 449 | 2.76 |
| (104) | −5.51 | — | 413 | 463 | 2.68 |
| (R02) | −5.63 | — | 411 | 469 | 2.64 |

Also from the measured values, it is found that P3Dic (abbreviation) and BP3Dic (abbreviation) have high HOMO levels. Further, it is found that P3Dic (abbreviation) and BP3Dic (abbreviation) have high T1 levels and can be used as a host material for a material emitting light in a visible light region.

Note that the thin films were cooled to 10 K and then irradiated with the excitation light to obtain emission spectra, which were calculated by a time-resolved method to find the peaks of phosphorescence. The T1 levels shown here are the values obtained by conversion from these peak values of phosphorescence to energy values.

REFERENCE NUMERALS

10: light-emitting layer, 11: first organic compound (host material), 12: second organic compound (guest material), 13: hole-transport layer, 14: host material, 101: anode, 102: cathode, 103: EL layer, 104: light-emitting layer, 105: first organic compound (host material), 106: second organic compound (guest material), 201: first electrode (anode), 202: second electrode (cathode), 203: EL layer, 204: hole-injection layer, 205: hole-transport layer, 206: light-emitting layer, 207: electron-transport layer, 208: electron-injection layer, 209: first organic compound (host material), 210: second organic compound (guest material), 301: first electrode, 302(1) to 302(n): EL layer, 304: second electrode, 305: charge-generation layer, 305(1) to 305(n-1): charge generation layer, 501: element substrate, 502: pixel portion, 503: driver circuit portion (source line driver circuit), 504a, 504b: driver circuit portion (gate line driver circuit), 505: sealant, 506: sealing substrate, 507: wiring, 508: FPC (flexible printed circuit), 509: n-channel TFT, 510: p-channel TFT, 511: switching TFT, 512: current control TFT, 513: first electrode (anode), 514: insulator, 515: EL layer, 516: second electrode (cathode), 517: light-emitting element, 518: space, 1100: substrate, 1101: first electrode, 1102: EL layer, 1103: second electrode, 1111: hole-injection layer, 1112: hole-transport layer, 1113: light-emitting layer, 1114: electron-transport layer, 1115: electron-injection layer, 7100: television device, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7301: housing, 7302: housing, 7303: joint portion, 7304: display portion, 7305: display portion, 7306: speaker portion, 7307: recording medium insertion portion, 7308: LED lamp, 7309: operation key, 7310: connection terminal, 7311: sensor, 7312: microphone, 7400: mobile phone, 7401: housing, 7402: display portion, 7403: operation button, 7404: external connection port, 7405: speaker, 7406: microphone, 8001: lighting device, 8002: lighting device, 8003: lighting device, 8004: lighting device, 9033: clip, 9034: switch for switching display modes, 9035: power button, 9036: switch for switching to power-saving mode, 9038: operation button, 9630: housing, 9631: display portion, 9631a: display portion, 9631b: display portion, 9632a: touch panel area, 9632b: touch panel area, 9633: solar battery, 9634: charge and discharge control circuit, 9635: battery, 9636: DCDC converter, 9637: operation key, 9638: converter, and 9639: button.

This application is based on Japanese Patent Application serial no. 2012-208080 filed with Japan Patent Office on Sep. 21, 2012, the entire contents of which are hereby incorporated by reference.

What is claimed is:

1. A light-emitting device comprising:
a pair of electrodes; and
a layer between the pair of electrodes, the layer comprising a compound and an iridium complex,
wherein the compound comprises two or more indolocarbazole rings condensed to one benzene ring and,
wherein an emission color of the iridium complex is blue.

2. The light-emitting device according to claim 1,
wherein each of the indolocarbazole rings is bonded to a substituted or unsubstituted phenylene group, and
wherein the substituted or unsubstituted phenylene group is bonded to any of a substituted or unsubstituted phenyl group, a substituted or unsubstituted pyridyl group, a substituted or unsubstituted pyrimidyl group, a substituted or unsubstituted naphthyl group, a substituted or unsubstituted fluorenyl group, a substituted or unsubstituted triphenylenyl group, and a substituted or unsubstituted phenanthrenyl group.

3. The light-emitting device according to claim 1,
wherein a difference between a HOMO level of the compound and a HOMO level of the iridium complex is lower than or equal to 0.3 eV.

4. A lighting device comprising the light-emitting device according to claim 1.

5. A light-emitting device comprising:
a pair of electrodes; and
a layer between the pair of electrodes, the layer comprising a compound represented by a formula (G1) and an iridium complex,

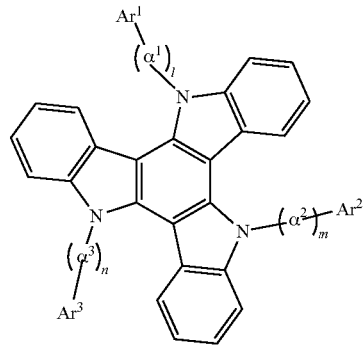

(G1)

wherein $\alpha^1$ to $\alpha^3$ independently represent a substituted or unsubstituted phenylene group or a substituted or unsubstituted biphenyldiyl group,
wherein $Ar^1$ to $Ar^3$ independently represent any of a substituted or unsubstituted phenyl group, a substituted or unsubstituted pyridyl group, a substituted or unsubstituted pyrimidyl group, a substituted or unsubstituted naphthyl group, a substituted or unsubstituted fluorenyl group, a substituted or unsubstituted triphenylenyl group, and a substituted or unsubstituted phenanthrenyl group,
wherein l, m and n are independently 0 or 1, and
wherein an emission color of the iridium complex is blue.

6. The light-emitting device according to claim 5, wherein one of the electrodes comprises ytterbium.

7. A lighting device comprising the light-emitting device according to claim 5.

8. A light-emitting device comprising:
a pair of electrodes;
a first layer between the pair of electrodes, the first layer comprising a first compound represented by a formula (G1); and
a second layer between the pair of electrodes, the second layer comprising a second compound represented by the formula (G1) and an iridium complex,

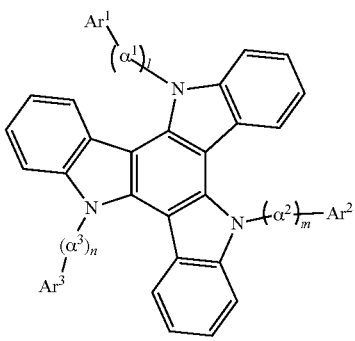

(G1)

wherein α¹ to α³ independently represent a substituted or unsubstituted phenylene group or a substituted or unsubstituted biphenyldiyl group, wherein Ar¹ to Ar³ independently represent any of a substituted or unsubstituted phenyl group, a substituted or unsubstituted pyridyl group, a substituted or unsubstituted pyrimidyl group, a substituted or unsubstituted naphthyl group, a substituted or unsubstituted fluorenyl group, a substituted or unsubstituted triphenylenyl group, and a substituted or unsubstituted phenanthrenyl group, and wherein l, m and n are independently 0 or 1.

9. The light-emitting device according to claim 8, wherein one of the electrodes comprises ytterbium.

10. The light-emitting device according to claim 8, wherein the first layer and the second layer are in contact with each other between the pair of electrodes.

11. The light-emitting device according to claim 8, wherein the first compound is different from the second compound.

12. The light-emitting device according to claim 8, further comprising:
a third layer between the first layer and the second layer, wherein the first layer further comprises an iridium complex, and
wherein the third layer comprises an aromatic amine compound and an electron acceptor.

13. The light-emitting device according to claim 12, wherein the aromatic amine compound comprises any one of NPB, TPD, TDATA, MTDATA, and 4,4'-bis[N-(spiro-9,9'-bifluoren-2-yl)-N-phenylamino]biphenyl, and
wherein the electron acceptor comprises any one of vanadium oxide, niobium oxide, tantalum oxide, chromium oxide, molybdenum oxide, tungsten oxide, manganese oxide, rhenium oxide, 7,7,8,8-tetracyano-2,3,5,6-tetrafluoroquinodimethane (abbreviation: $F_4$-TCNQ), and chloranil.

14. The light-emitting device according to claim 12, wherein the third layer comprises a metal complex and an electron donor.

15. The light-emitting device according to claim 14, wherein the metal complex comprises any one of Alq, Almq₃, BeBq₂, BAlq, Zn(BOX)₂ or Zn(BTZ)₂, PBD, OXD-7, TAZ, BPhen, and BCP, and
wherein the electron donor comprises any one of lithium (Li), cesium (Cs), magnesium (Mg), calcium (Ca), ytterbium (Yb), indium (In), lithium oxide, cesium carbonate, and tetrathianaphthacene.

16. The light-emitting device according to claim 12, further comprising:
a fourth layer between the pair of electrodes, the fourth layer comprising a third compound and an iridium complex,
the third layer between the first layer and the second layer; and
a fifth layer between the second layer and the fourth layer, wherein the first layer further comprises an iridium complex, and
wherein the fifth layer comprises the aromatic amine compound and the electron acceptor.

17. The light-emitting device according to claim 16, wherein the fifth layer comprises a metal complex and an electron donor.

18. A lighting device comprising the light-emitting device according to claim 12.

* * * * *